(12) United States Patent
Chen et al.

(10) Patent No.: US 11,541,006 B2
(45) Date of Patent: Jan. 3, 2023

(54) AQUEOUS FORMULATION FOR INSOLUBLE DRUGS

(71) Applicant: Andrew Xian Chen, San Diego, CA (US)

(72) Inventors: Andrew Xian Chen, San Diego, CA (US); Jan-Jon Chu, Carlsbad, CA (US); Jianmin Xu, San Diego, CA (US); Mohammad Saiful Islam, Poway, CA (US)

(73) Assignee: Andrew Xian Chen, San Diego, CA (US)

( * ) Notice: Subject to any disclaimer, the term of this patent is extended or adjusted under 35 U.S.C. 154(b) by 0 days.

(21) Appl. No.: 16/993,017

(22) Filed: Aug. 13, 2020

(65) Prior Publication Data

US 2020/0368159 A1    Nov. 26, 2020

Related U.S. Application Data

(63) Continuation of application No. PCT/US2019/021029, filed on Mar. 6, 2019.

(60) Provisional application No. 62/639,710, filed on Mar. 7, 2018.

(51) Int. Cl.

| | | |
|---|---|---|
| *A61K 9/08* | (2006.01) | |
| *A61K 47/14* | (2017.01) | |
| *A61K 47/24* | (2006.01) | |
| *A61K 47/28* | (2006.01) | |
| *A61K 9/00* | (2006.01) | |
| *A61K 45/06* | (2006.01) | |

(52) U.S. Cl.
CPC ............ *A61K 9/08* (2013.01); *A61K 47/14* (2013.01); *A61K 47/24* (2013.01); *A61K 47/28* (2013.01); *A61K 9/0019* (2013.01); *A61K 45/06* (2013.01)

(58) Field of Classification Search
None
See application file for complete search history.

(56) References Cited

U.S. PATENT DOCUMENTS

| | | |
|---|---|---|
| 4,649,155 A | 3/1987 | Steffen et al. |
| 6,193,985 B1 | 2/2001 | Sonne |
| 6,586,407 B1 | 7/2003 | Bruzzese et al. |
| 2002/0107291 A1 | 8/2002 | De Tommaso |
| 2004/0052845 A1 | 3/2004 | Appel et al. |
| 2015/0224121 A1 | 8/2015 | Okumu et al. |
| 2015/0272943 A1 | 10/2015 | Kim et al. |

FOREIGN PATENT DOCUMENTS

| | | |
|---|---|---|
| EP | 0391369 A2 | 10/1990 |
| WO | 2009/046444 A2 | 4/2009 |

OTHER PUBLICATIONS

Egg Phosphatidylcholine [online]. Creative Biolabs Mar. 8, 2022 [retrieved on Mar. 8, 2022], Retrieved from the internet: <https://www.creative-biolabs.com/lipid-based-delivery/egg-phosphatidylcholine.htm#:~:text=Egg%20yolk%20lecithin%20contains%2078, which%20depends%20on%20the%20source.>. (Year: 2022).*

Application No. PCT/US2019/021029, International Preliminary Report on Patentability, dated Sep. 17, 2020, 10 pages.

Application No. PCT/US2019/021029, International Search Report and Written Opinion, dated May 8, 2019, 12 pages.

Cai et al., "A Propofol Microemulsion with Low Free Propofol in the Aqueous Phase: Formulation, Physicochemical Characterization, Stability and Pharmacokinetics," International Journal of Pharmaceutics, vol. 436, No. 1-2, Oct. 1, 2012, pp. 536-544.

Application No. EP19764228.3, Extended European Search Report, dated Dec. 7, 2021, 9 pages.

* cited by examiner

*Primary Examiner* — Katherine Peebles
(74) *Attorney, Agent, or Firm* — Kilpatrick Townsend & Stockton LLP

(57) ABSTRACT

This invention relates to clear one-phase liquid formulation vehicles comprising lecithin, MCT, bile salt and water.

19 Claims, 8 Drawing Sheets

AQUEOUS FORMULATION FOR INSOLUBLE DRUGS

CROSS-REFERENCE TO RELATED APPLICATIONS

This application is a continuation of PCT Application No. PCT/US2019/021029, filed Mar. 6, 2019, which claims priority to U.S. Provisional Application No. 62/639,710, filed Mar. 7, 2018, the disclosures of which are hereby incorporated by reference in their entirety for all purposes.

FIELD OF THE INVENTION

This invention relates to clear and one-phase aqueous solution compositions comprising lecithin, medium chain triglycerides, a bile salt and water having utility as formulation vehicles to dissolve drugs for pharmaceutical applications.

BACKGROUND OF THE INVENTION

Insoluble molecules account for about 40-60% of drug substances now being discovered or commercially developed. To be suitable for injection as well as many other routes of administration, these drugs must first be dissolved in a liquid vehicle. For safety reasons, an aqueous vehicle is preferred over a non-aqueous vehicle.

Various drug solubilizers have been developed to dissolve insoluble drugs, including those that use lecithin, oils, bile salts or cyclodextrins. All these prior art solubilizers have one or more of the following drawbacks, namely:
1. Not a clear or one-phase solution,
2. Unable to dissolve many drugs to be considered of general utility,
3. Require high energy to dissolve the drug,
4. Drug precipitates when diluted with water or an IV infusion fluid, and
5. Poor safety when injected into human or animals.

The present invention relates to four-component solution compositions comprising Lecithin, Medium chain triglycerides (MCT), a Bile salt, and Water, which are herein referred to as L, M, B, and W, respectively, in this application. For convenience, a composition of this invention is also referred to herein as an LMBW formulation, an LMBW composition or an LMBW.

An LMBW composition has certain physical and biological properties that are very useful for drug formulations, especially for insoluble drugs. An LMBW composition is free of the aforementioned drawbacks associated with other solubilizers.

BRIEF SUMMARY OF THE INVENTION

This disclosure provides a clear one-phase aqueous solution composition, comprising, consisting essentially of, or consisting of:
a. lecithin;
b. MCT;
c. bile salt; and
d. water.

In an aspect, this invention provides a clear and one-phase aqueous liquid composition, comprising:
a. lecithin at a concentration between about 6% and about 72.5%;
b. MCT at a concentration between 0% and about 32.5%;
c. bile salt at a concentration between about 11.5% and about 94%;
wherein the water is at a concentration no less than about 0.1/1 (w/w) in weight ratio of water to the total weight of lecithin, MCT and bile salt, where the % is the weight percentage (w/w) over the total weight of the lecithin, MCT and bile salt.

In an aspect, this invention provides a clear and one-phase aqueous liquid composition comprising: a lecithin, MCT, bile salt, and water, in a four-component LMBW composition, their preparation and applications in drug formulations.

In an aspect, the LMBW composition provided in this invention is a one-phase solution and is not a multiple-phase system such as emulsion, liposome, mixed micelle dispersion and suspension.

In an aspect, the LMBW composition provided in this invention is a formulation vehicle without a drug.

In an aspect, the LMBW composition provided in this invention further contains a drug, cosmetic agent, diagnostic agent, or nutritional supplement (i.e., an active ingredient).

In an aspect, the LMBW composition provided in this invention contains an insoluble or a soluble drug.

In an aspect, the LMBW composition provided in this invention further contains an excipient including, but not limited to, an alcohol, preservative, antioxidant, bulking agent, or a mixture thereof.

This invention also provides a method to increase the solubility of an insoluble drug using an LMBW composition as a liquid vehicle, a solubilizer or solubility enhancer.

In an aspect, the LMBW composition provided in this invention is between pH 3 and pH 10.

This invention also provides a method to make an LMBW composition.

This invention also provides a method to make an LMBW composition without water or substantially-free of water.

In yet another aspect, this invention provides a method as a diagnostic, treatment or prophylaxis for a patient by administration of an LMBW composition with or without a drug.

In an aspect, the LMBW compositions provided in this invention are for medicinal, cosmetic or nutrition supplement application.

In an aspect, the LMBW composition provided in this invention is used to increase solubility of a drug in water.

In an aspect, the LMBW compositions are suitable for injection or for oral, topical, inhalation, ophthalmic, otic, intranasal, intravaginal administration, or other routes of administration in a human or animal patient.

These and other aspects, objects and embodiments will become more apparent when read with the detailed description and figures which follow.

BRIEF DESCRIPTION OF THE DRAWINGS

FIG. 7 illustrates a Solid LMBW (F95, Example 28), which is transparent, amorphous and glass-like.

DETAILED DESCRIPTION OF THE INVENTION

I. DEFINITIONS

Figure 1:
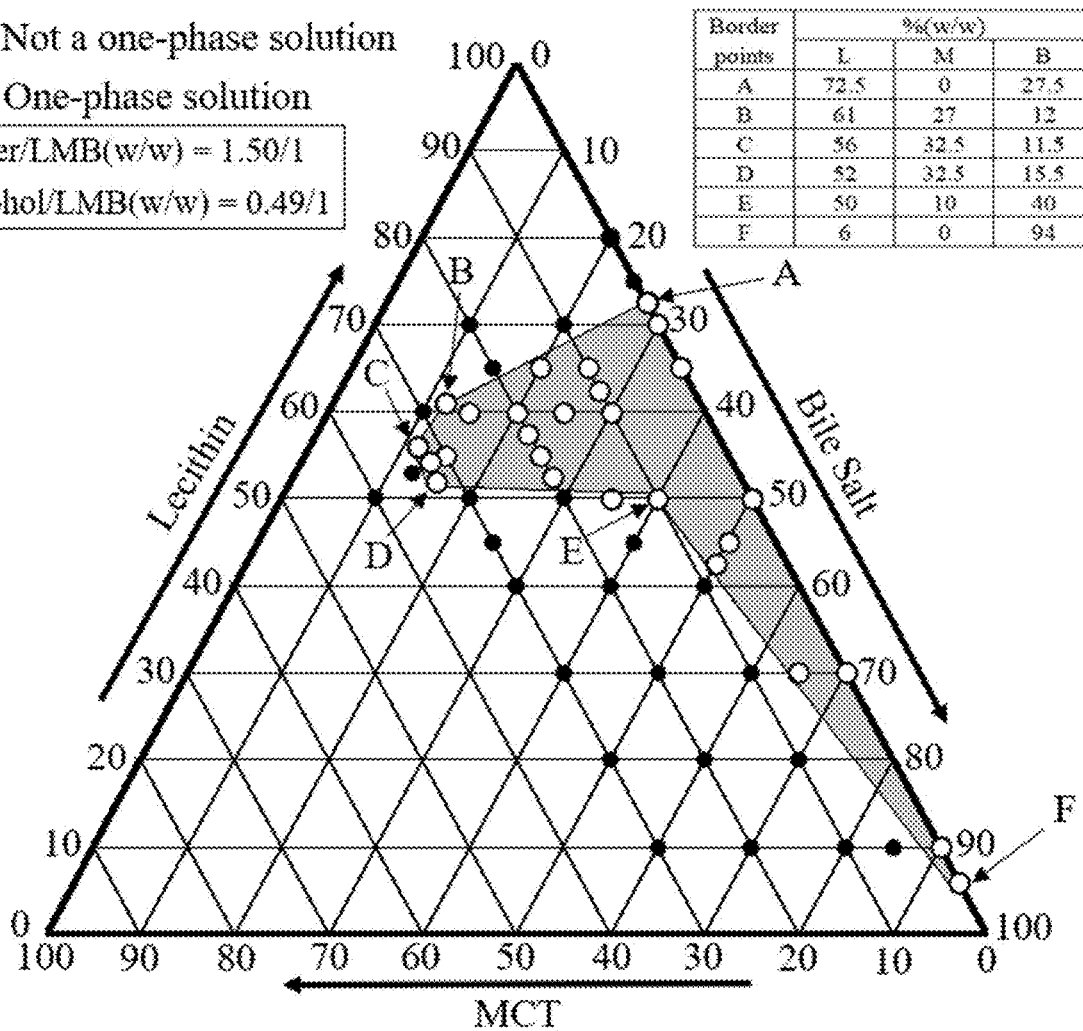
FIG. 1 illustrates a ternary phase diagram in an equilateral triangle plot graphically depicting concentrations (in % w/w based on the Dry Weight or combined weight of L, M and B) of the three components (L, M and B) in combinations with a fixed amount of water according to the present invention.
Figure 2:
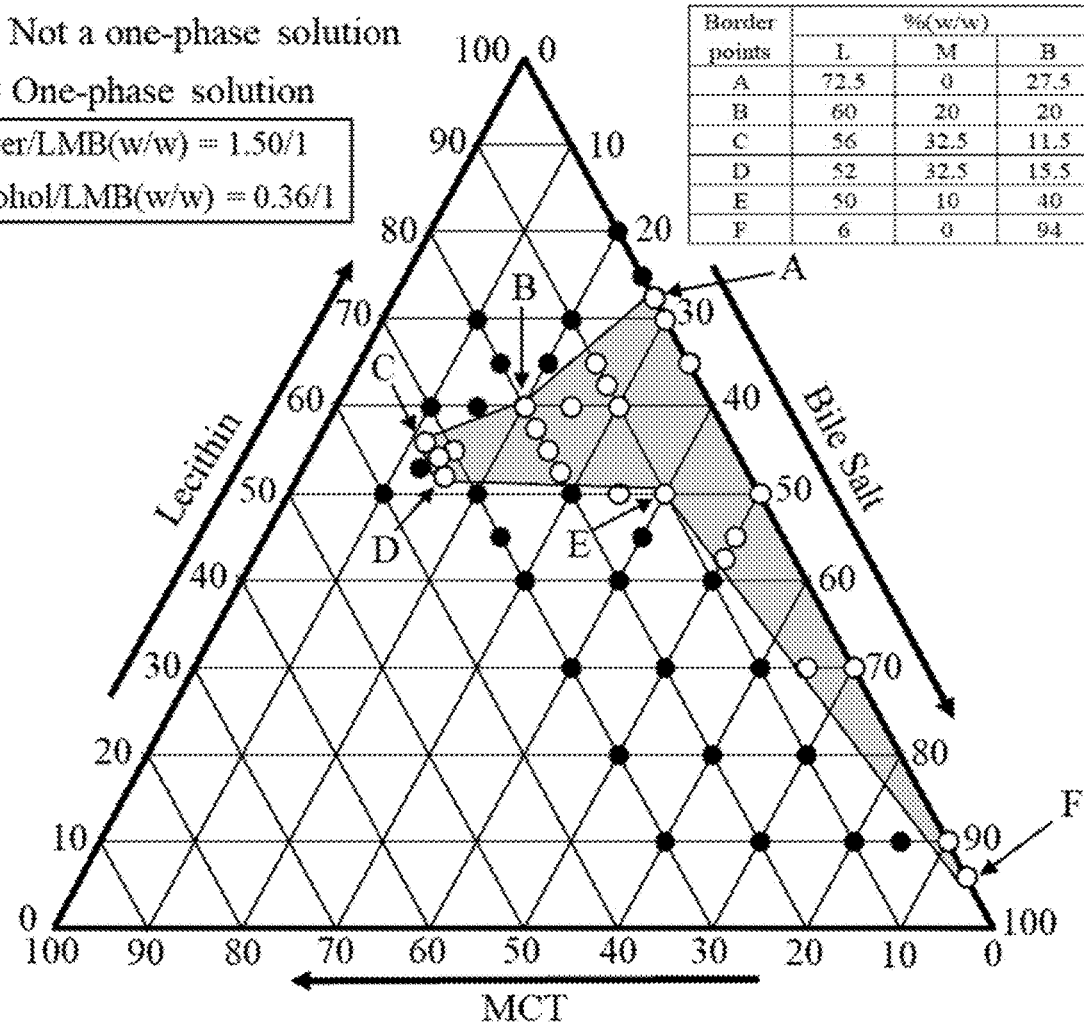
FIG. 2 illustrates a ternary phase diagram in an equilateral triangle plot graphically depicting concentrations (in % w/w based on the Dry Weight or combined weight of L, M and B) of the three components (L, M and B) in combinations according to the present invention.
Figure 3:
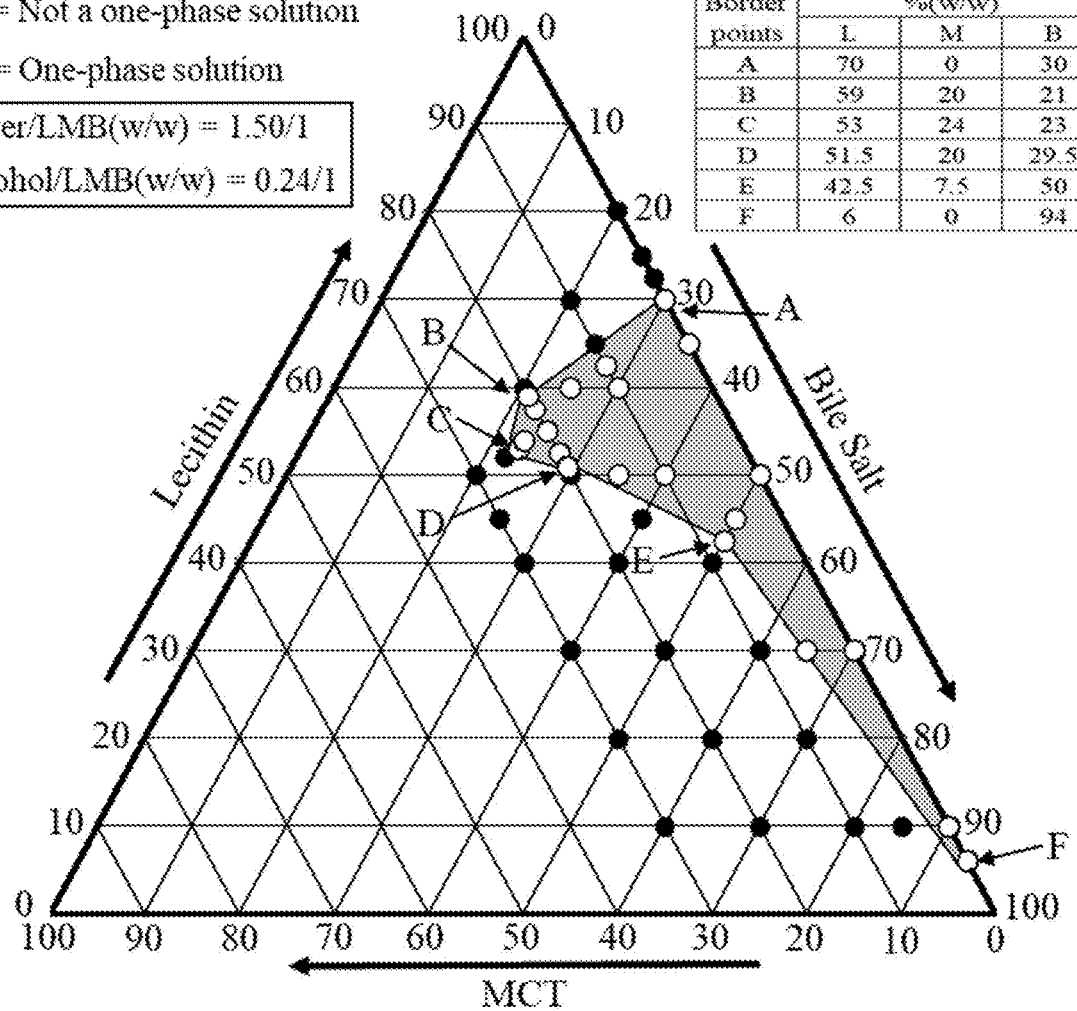
FIG. 3 illustrates a ternary phase diagram in an equilateral triangle plot graphically depicting concentrations (in % w/w based on the Dry Weight or combined weight of L, M and B) of the three components (L, M and B) in combinations with a fixed amount of water according to the present invention.

The various terms used herein shall have the following definitions:

As used herein, "about" describes a quantity with a range covering 10% expansion from both sides of the target value. For example, "about 100" means any value between 90 and 110, including 90 and 110 such as 90, 91, 92, 93, 94, 95, 96, 97, 98, 99, 100, 101, 102, 103, 104, 105, 106, 107, 108, 109, and/or 110 and fractions in-between.

As used herein, an "acid" refers to any organic or inorganic acid that is suitable for pharmaceutical use. Acids that have previously been approved by the FDA for use in injectable or other solution-based drugs, or are listed on the FDA's Inactive Ingredient List, are preferred. Acids that are particularly useful for an LMBW include, but are not limited to, acetic acid, ascorbic acid, aspartic acid, benzenesulfonic, benzoic acid, citric acid, formic acid, fumaric acid, hydrochloric acid, hydrobromic acid, lactic acid, lactobionic acid, maleic acid, malic acid, malonic acid, methanesulfonic acid, phosphoric acid, propionic acid, succinic acid, sulfuric acid, and tartaric acid.

An "antioxidant" is a pharmaceutical additive that can be added to a liquid composition to prevent oxidation of the drug molecule or an inactive component. Antioxidants include, but are not limited to, reducing agents, metal ion chelating agents and inert gases. The preferred antioxidants for an LMBW include, but are not limited to, EDTA, citric acid, glycine, butylated hydroxyanisole, butylated hydroxytoluene, cysteine, methionine, thioglycerol, bisulfite, metabisulfate, ascorbate, propyl gallate, tocopherol, reducing sugar, or salt or mixture thereof.

As used herein, "aqueous" means that the composition is made with water as the main solvent with its concentration greater than the concentration of any other liquid solvent.

As used herein, "alcohol" is an organic solvent in which one hydroxyl functional group (—OH) is bound to a carbon atom and this carbon is saturated, having single bonds to three other atoms. In an LMBW, an Alcohol is an excipient added primarily to increase solubility of a drug. The alcohols useful for an LMBW are ethanol, benzyl alcohol, propylene glycol, polyethylene glycol of a low molecular weight (100-5,000) or a combination thereof.

As used herein, the term "Alcohol to Dry Weight Ratio" or "Alcohol/LBM" refers to the ratio of Alcohol weight to the Dry Weight in an LMBW. For example, for an LMBW composition comprising 61 g lecithin, 21 g MCT, 18 g bile salt and 49 g alcohol, the Dry Weight is 100 g (=61 g+21 g+18 g) and the Alcohol to Dry Weight Ratio or Alcohol/LBM is 49/100 or 0.49/1.

As used herein, a "base" is an alkalizing agent used to adjust the pH of an LMBW. Both organic and inorganic bases can be used. The preferred bases include, but are not limited to, sodium hydroxide, potassium hydroxide, calcium hydroxide, ammonium hydroxide, lysine, arginine, or a combination thereof.

As used herein, a "bile salt" or "B" used in an LMBW composition refers to an alkali salt, such as sodium salt, of cholic acid, glycocholic acid, taurocholic acid, deoxycholic acid, glyco- or taurodeoxycholic acid, chenodeoxycholic acid and glyco- or taurochenoxydeoxycholic acid. Sodium glycocholate and sodium deoxycholate are preferred bile salts. Other cations including, but not limited to, potassium, lithium, calcium, arginine, lysine or ammonium salt may also be used in a bile salt. For use in an LMBW, either a bile acid or a bile salt can be used as a starting material. If a bile acid is used as the starting material, it is usually converted (completely or partially) to its bile salt (i.e., the conjugate base) by adjusting pH upward before or during the preparation of an LMBW. If a bile salt is used as the starting material, it may be converted (completely or partially) to its bile acid (i.e., the conjugate acid) by adjusting pH downward during the preparation of an LMBW. In one aspect, the term "bile salt" or "B" used in this application also refers to a mixture of a bile salt and its conjugate acid. For example, the pKa of deoxycholic acid is 6.58 (The Merck Index, $12^{th}$ Ed., Entry #12946). According to the Henderson-Hasselbalch equation, a solution of deoxycholic acid in water at pH 4.58 would contain a mixture of 99% protonated deoxycholic acid (bile acid) and 1% deprotonated deoxycholate (bile salt). Such a bile acid/bile salt mixture is well suited for use in an LMBW. For clarity, concentration of a bile salt used in an LMBW is provided herein as the concentration of the conjugate bile acid.

As used herein, a "Border point" refers to an LMBW composition which is very close to a non-LMBW composition in a ternary phase diagram (Example, FIGS. 1-5). Each Border point is experimentally determined and is used together with other Border points to map out the "LMBW zone" within which all compositions are clear and one-phase, i.e. an LMBW, in the ternary phase diagram.

A "bulking agent" of this invention refers to an excipient that is added to an LMBW composition to protect its components during and after freezing or drying (usually by lyophilization) and to provide the solid bulk after the drying. The bulking agents that are useful for an LMBW include, but are not limited to, monosaccharides, disaccharides, polysaccharides, propylene glycols, polyethylene glycols, glycerols, poly-ols, dextrins, cyclodextrins, starches, celluloses and cellulose derivatives, proteins, peptides, amino acids, sodium chloride, polyvinylpyrrolidone, or mixtures thereof. The preferred bulking agent for an LMBW is a carbohydrate such as mannitol, sorbitol, xylitol, lactose, fructose, xylose, sucrose, trehalose, mannose, maltose, dextrose, dextran, or a mixture thereof. The concentration of the bulking agent useful in an LMBW may be from about 1% to about 30% w/w, preferably, from about 2% w/w to about 10% w/w or more preferably, from about 3% w/w to 8% w/w, based on weight of the LMBW composition.

As used herein, the terms "clear" and "transparent" are used herein interchangeably and mean that the composition has a light transmittance value measured at 800 nm light wavelength (T800) using a 10-mm quartz cuvette by a UV-vis spectrophotometer exceeding 70%, preferably 80% and more preferably 90%.

With such high light transmittance, it is possible to see through the clear composition in a clear glass vial, which allows for examination of presence of foreign particles (e.g. broken glass or metal particles) or other abnormal defects (e.g. microbial growth) that are unsafe for injection. In contrast, a multiple-phase injectable composition such as DIPRIVAN® (emulsion with T800 value of less than 10%) and EXPAREL® (liposome with T800 value of less than 70%) are white, opaque or hazy liquid and do not permit good visual examination for the harmful foreign particles. For pharmaceutical use, a clear and one-phase solution is preferred over a cloudy and multiple-phase composition.

As used herein and unless otherwise stated, the term "concentration" refers to the weight percent concentration based on the Dry Weight in a composition of interest. For example, for a composition containing 20 g of L, 6 g of M and 11 g of B, the Dry Weight is 37 g (=20+6+11) and the concentrations for L, M and B, are 54.1% (=20/37), 16.2% (=6/37) and 29.7% (=11/37), respectively.

As used herein, diazepam, also known as Valium®, is a medicine of the benzodiazepine family that typically produces a calming effect. It is commonly used to treat a range of conditions including anxiety, alcohol withdrawal syndrome, benzodiazepine withdrawal syndrome, muscle spasms, seizures, trouble sleeping, and restless legs syndrome. It is used in emergency situations to stop cluster seizures (episodes of increased seizure activity). A diazepam rectal gel (Diastat®) is approved by the FDA for this emergency or rescue use, but the rectal gel is inconvenient to use. A ready-to-use and preferable self-administered injection is a better dosage form. Diazepam is very insoluble in water, the currently marketed diazepam injection formulation (Diazepam Injection, USP) can dissolve only about 5 mg/mL diazepam. For the seizures rescue dose of 20 mg, a 4-mL injection volume would be required if the current marketed formulation is used, which is too much volume for intramuscular or subcutaneous injection. Therefore, there is a need to develop a new injectable diazepam formulation, which can significantly increase diazepam solubility and allow for delivery of 20 mg diazepam in about 1-2 mL volume. An LMBW composition capable of solubilizing diazepam to 17 mg/mL and delivering 20 mg in 1.2 mL volume was thus developed and tested in human with excellent safety outcomes (Example 25).

As used herein, the "drug" means any chemical that is biologically active.

As used herein, the phrase "Dry Weight" refers to the total weight of L, M and B in a composition of interest in this invention. Dry Weight does not include any other component that may also be present in the composition. For example, for a composition containing 61 g L, 21 g M, 18 g B, 50 g alcohol, 1 g preservative, 1 g antioxidant and 150 g water, the Dry Weight is 100 g (=61+21+18). Dry Weight is used as the weight base to calculate the weight percent concentration of L, M or B in a composition of interest in this invention.

As used herein, an "excipient" refers to a biologically inactive substance that serves various functions in a drug formulation such as a vehicle, medium, stabilizer, preservative etc. An LMBW is a uniquely defined combination of 4 excipients (L, M, B and W). Other excipients useful in an LMBW may include but not limited to alcohol, pH buffer, osmotic adjusting agent, preservative, antioxidant, bulking agent.

As used herein, an "emulsion" is a mixture of two liquids that are normally immiscible (unmixable or having two phases). In an emulsion, one liquid (the dispersed phase) is dispersed in the other (the continuous phase). Two liquids can form different types of emulsions. As an example, oil and water can form, first, an oil-in-water emulsion, wherein the oil is the dispersed phase, and water is the dispersion phase. Second, they can form a water-in-oil emulsion, wherein water is the dispersed phase and oil is the dispersion phase. For injectable drug formulations, the oil-in-water type is more common. In an oil-in-water emulsion, the oil phase exists as small oil droplets in 50-5000 nm diameter suspended in water (the aqueous phase). For example, the droplet size of the injectable emulsion drugs DIPROVAN® (Propofol emulsion for injection) and INTRALIPID® are about 150-500 nm in diameter, both contain lecithin and oil, and both are white and opaque with T800 less than 10%. The LMBW compositions of the present invention are not emulsions.

As used herein, "formulation" refers to a mixture of excipients or other chemicals prepared according to a specific recipe and preparation procedure. A formulation constitutes the final or intermediate form of a drug, cosmetic or supplement product, such as tablet, capsule, lotion etc. A formulation may optionally contain a drug. The terms of "composition" and "formulation" are used interchangeably in this application.

As used herein, "FDA" refers to the U.S. Food and Drug Administration.

As used herein, "filterable" means the ability of a liquid to pass through a filter membrane of a certain pore size such as 0.2 microns. The LMBW compositions of the present invention are filterable.

The term of "high-energy homogenization" used herein refers to any homogenization method using equipment, which employs high-pressure or ultrasonification mechanism, to render particle reduction and mixing. A high-pressure homogenizer works by using a high pressure (e.g. >10,000 psi) to force a liquid sample through a small channel to generate high shear effect, which breaks up the particles or oil into small particle/droplets. Examples of high-pressure equipment include, but not limited to, microfluidizers, APV homogenizers, Gaulin homogenizers and Rannie homogenizers. Ultrasonification homogenizer, referred herein, may include probe type or bath type. The formation of LMBW compositions of the present invention does not need high-energy homogenization.

The "low energy mixer" used herein refers to a rotational stirrer operating at a speed of less than 5000 RPM or a one- or multi-dimensional shaker operating at frequency of less than 5000 cycles per minute. The rotational stirrer may include, but not limited to, a simple propeller or impeller type mixer or a rotor-stator type of high shear mixer. A high shear mixer uses a rotating impeller or high-speed rotor, or a series of such impellers or inline rotors, usually powered by an electric motor, to "work" the fluid, creating flow and shear. A stationary component may be used in combination with the rotor and is referred to as the stator. The stator creates a close clearance gap between the rotor and itself and forms a high shear zone for the material as it exits the rotor. The formation of LMBW compositions of the present invention may be facilitated by a low energy mixer.

As used herein, the word "injectable", or phrase "suitable for injection" refers to a formulation that can be injected through a hypodermic needle safely into human or animal patients when (1) each of the components in the formulation has been used in a marketed injection drug approved by the FDA at the time of this application, (2) the formulation can be expelled manually using a syringe through a needle smaller than 21 gauge, preferably 25 gauge and more preferably 27 gauge, (3) the formulation is free of any particles of size >10 micron in diameter, and (4) the viscosity of the formulation is less than 10,000 centipoises, preferably less than 1,000 centipoises and more preferably less than 100 centipoises.

As used herein, the word "injection" means insertion of liquid into the body via a hypodermic needle into one or more different locations that include, but are not limited to, intravenous, intra-arterial, subcutaneous, intramuscular, intradermal, intracavernous, intracavitary, intravesical, interstitial, intra-articular, intradermal, intrabursal, intralesional, intratumor, intraperitoneal, intrapleural, intrasynovial, intrathecal, and intratracheal, or via infiltration, nerve block, IV infusion, or other route of injection.

As used herein, an "insoluble drug" refers to a drug or pharmacologically active agent lacking solubility in aqueous solutions (such as water, physiological saline, injectable dextrose solutions, etc.). The USP/NF generally expresses the solubility in terms of the volume of solvent required to dissolve 1 gram of the pharmacologically active agent at a specified temperature (e.g., 1 g aspirin in 300 ml water, 5 ml ethanol at 25° C.). Other references may use more subjective terms to describe solubility, such as those given in the following table from Remington's Pharmaceutical Sciences, Mack Publishing Co., Easton, Pa., latest edition.

| Descriptive terms | Parts of solvent needed for 1 part solute |
|---|---|
| Very soluble | <1 |
| Freely soluble | 1-10 |
| Soluble | 10-30 |
| Sparingly soluble | 30-100 |
| Slightly soluble | 100-1000 |
| Very slightly soluble | 1000-10,000 |
| Practically insoluble or insoluble | >10,000 |

Thus, as used herein, an "insoluble drug" of this invention includes any drug whose solubility would place it in the bottom four solubility categories in the above table, i.e., "sparingly soluble," "slightly soluble," "very slightly soluble," and "practically insoluble or insoluble," when water is used as the solvent. As used herein, the word "insoluble" may be used interchangeably with hydrophobic, lipophilic, oleophilic, and other similar terms. Examples of insoluble drugs that can be dissolved by an LMBW include, but are not limited to amiodarone, amphotericin, aprepitant, camptothecin, clarithromycin, cyclosporine, diazepam, docetaxel, ibuprofen, celecoxib, itraconazole, irinotecan, iodine, levodopa, paclitaxel, phytonadione, posaconazole, prednisolone acetate, progesterone, propofol, resveratrol, and voriconazole.

As used herein, the phrase "IV infusion fluids" refer to the sterile aqueous solutions commonly used to dilute a drug for intravenous infusion. Examples of IV infusion fluids useful to dilute an LMBW include, but are not limited to, 5% Dextrose Injection, USP, 5% Dextrose Injection, USP and 0.9% Sodium Chloride Injection, USP, Lactated Ringer's Injection, USP, 5% Dextrose and Lactated Ringer's Injection, USP, Normosol-M and 5% Dextrose, 0.9% Sodium Chloride Injection, USP, and ISOLYTE E.

As used herein, the phrase "laser light scattering" or "dynamic light scattering (DLS)" is a technique in physics that can be used to determine the size distribution profile of small particles in liquid, including proteins, polymers, micelles, mixed micelles, liposomes, emulsions, vesicles, carbohydrates, nanoparticles, biological cells and gels. A DLS is one of the most sensitive tools to detect small particles. For example, with a sizing range between 0.6 nm to 10 microns, the DLS spectrometry used to examine the LMBW composition (see Example 13 & Example 16 Malvern Zetasizer, Model Nano-ZS) is capable of detecting any nanometer- and micrometer-sized particles, droplets or supramolecular assembly such as liposomes, emulsions, micelles, mixed micelles or nanoparticles.

As used herein, "long chain triglycerides" or "LCT" are tri-esters of glycerol with saturated and unsaturated fatty acids having long chains of 18 to 24 carbons in length. LCTs are found in most foods and are abundant in nature. LCTs are the main components of vegetable oils such as sesame oil, soybean oil, corn oil, safflower oil, castor oil, olive oil, etc. Interestingly, it was discovered by the inventors that LCT or a vegetable oil such as sesame oil cannot form an LMBW. Thus, in the present invention, the MCT cannot be replaced by an LCT.

As used herein, "lecithin" or "L" is a mixture of phospholipids derived from a natural source. Injectable lecithin includes lecithin which has been derived from eggs, soybeans, sunflower seeds or other natural sources, further purified and is substantially free from proteins or other irritating, allergenic, inflammatory agents or agents that cause other deleterious biological reactions. For this invention, the preferred lecithin includes those that contain more than 75% (w/w over the total weight of lecithin) phosphatidylcholine (PC). Examples of the preferred lecithin include, but are not limited to, commercial lecithin products going by the trade names of LIPOID S 75, LIPOID S 100, LIPOID E 80, and Phospholipon 90 G. Lecithin useful for an LMBW composition may also include synthetic phospholipids, preferably a PC or a mixture of synthetic phospholipids having more than 75% (w/w over the total weight of the mixture) PC.

The term "light transmittance (%)" used herein is a measurement of transparency of a liquid and is defined as the fraction of incident light at a specified wavelength (i.e., 800 nm or lambda) that passes through a sample contained in a transparent cuvette (e.g. a quartz cuvette with 10 mm path length). It is calculated using the following equation:

$$T_{(lambda)} = I \div I_0 \times 100$$

where $I_0$ is the intensity of the incident light and I is the intensity of the light coming out of the sample and $T_{(lambda)}$ is transmittance at the wavelength lambda. The $T_{(lambda)}$ value can be readily measured by a UV-visible spectrophotometer at a fixed wavelength. For the clear compositions of this invention, T800 is a $T_{(lambda)}$ value measured at 800 nm in a quartz cuvette with 10 mm path length using a UV-visible spectrophotometer.

As used herein, a "liposome" is a spherical nanometer- and micrometer-sized solid particle having a bilayer membrane formed by lecithin or phospholipid molecules. The self-organizing bilayer membranes are the characteristic structural feature of liposomes. Liposomes are most often composed of phospholipids, especially phosphatidylcholine, but may also include other lipids, such as egg phosphatidylethanolamine, so long as they are compatible with lipid bilayer structure. The major types of liposomes are the multilamellar vesicle (MLV, with several lamellar phase lipid bilayers), the small unilamellar liposome vesicle (SUV, with one lipid bilayer), the large unilamellar vesicle (LUV), and the cochleate vesicle. Liposomes should not be confused with micelles or mixed micelles which are composed of monolayers. A liposome particle size can range from 20 nm to 40 µm in diameter. For example, the liposome particle size in the liposome drugs AmBisome®, Doxil®, Caelyx® and EXPAREL® are reportedly 77.8 nm, 80-85 nm, 80-85 nm and 24-31 µm, respectively. A liposome formulation or liposome composition is often referred to an aqueous suspension of the liposome particles. Clearly, the liposome formulation or liposome composition is a 2-phase system and is usually hazy or not clear in appearance due to the presence of the particles. The LMBW compositions of the present invention are not liposomes.

As used herein, an "LMBW" refers to a composition comprising Lecithin, Medium chain triglyceride (MCT), and Bile salt constructed in quantities within an LMBW Zone.

As used herein, the term "LMBW Properties" refers to the following desirable basic physical and biological properties of an LMBW that include being (1) a clear and one-phase solution, (2) capable of dissolving insoluble drugs of widely different structures, i.e. a Universal Solubilizer, (3) spontaneously self-forming in water (i.e., does not require high-energy homogenization for its preparation), (4) can be further diluted in water or an IV infusion fluid without any precipitation or phase separation i.e., remains as one-phase solution after being diluted with water, and (5) injectable.

As used herein, an "LMBW zone" refers to a zone in a ternary phase diagram having L, M, B in various combinations and water at a fixed water to Dry Weight Ratio. The LMBW zones were experimentally determined and systematical mapped out by the inventors of this application. Examples of LMBW zones are graphically shown in FIGS. 1-5. An LMBW zone is used to define the upper and lower concentration limits for each of the L, M and B components. Only within the LMBW zone, a mixture of L, M and B can form a clear and one-phase solution in water or an LMBW.

As used herein, a "Medium Chain Triglycerides", "MCT" or "M", which are also known as "medium chain triglyceride oil" are tri-esters of glycerol with fatty acids having medium length chains of 6 to 12 carbons in length. An MCT can be either derived from a natural source or made synthetically. Natural MCT is commonly derived from coconut oil and contains a mixture of glyceryl tri-esters of fatty acids with different chain lengths (6-12 carbons $C_6$, $C_7$, $C_8$, $C_9$, $C_{10}$, $C_{11}$ and/or $C_{12}$), or mono-, di- and tri-glycerides. Examples of the natural MCT include commercial products with the trade names CRODAMOL GTCC-PN, Miglyol 812, CAPMUL MCM and Neobees M-5. A synthetic MCT may contain essentially one molecule. Examples of synthetic MCT may include, but are not limited to, glyceryl tri-esters of propionic acid, butyric acid, valeric acid, caproic acid, enanthic acid, caprylic acid, pelargonic acid, capric acid or the mixture thereof. Examples of the preferred MCTs for an LMBW include Miglyol 812 and synthetic triglycerides having 6, 8, 10 or 12 carbon fatty acids.

As used herein, a "micelle" is an aggregate or supramolecular assembly with single layer membranes of surfactant molecules dispersed in a liquid such as water. A typical micelle in aqueous solution forms an aggregate with the hydrophilic "head" regions in contact with water, sequestering the hydrophobic single-tail regions in the micelle center. Micelles are generally formed by water soluble surfactant with an HLB or Hydrophilic-Lipophilic Balance value greater than 7. Lecithin alone generally cannot form micelles in water because it is insoluble in water (it forms liposome, solid lipid particles or emulsion when combined with oil). However, when combined with a water-soluble surfactant, lecithin can form mixed micelles in water.

As used herein, a "mixed micelle" is an aggregate or supramolecular assembly with single layer membranes of lecithin by incorporating itself into a water-soluble surfactant micelle in water. Mixed micelles made with combination of a bile salt (which is a water-soluble surfactant) and lecithin have been used to solubilize drugs. For example, VALIUM® MM (diazepam injection) and KONAKION® MM (vitamin K injection) are lecithin-bile salt based mixed micelle (MM) formulation. The particle size of the lecithin-bile salt mixed micelles has been reported to be about 8 nm or greater in diameter as measured by various analytical techniques including laser light scattering (J. Wylie Nichols and Justyna Ozarowski, "Sizing of lecithin-bile salt mixed micelles by size-exclusion high-performance liquid chromatography" Biochemistry 1990, 29, 4600-4606), or an average size from ~5 nm to ~14 nm depending upon the bile salt concentration as confirmed by another group of researchers (Biochimica et Biophysica Acta 1808 (2011) 140-153). Unlike an LMBW which is a one-phase solution, presence of these 5 nm or greater particles in a mixed micelle composition clearly indicate that it is not a one-phase solution.

As used herein, an "osmotic adjusting agent" refers to an ingredient added to a composition of this invention to increase its osmotic pressure. An LMBW may have an osmotic pressure of approximately 100 to 1000 mOsm with the preferred range of 200 to 400 mOsm such as 225, 250, 275, 300, 325, 350, or 400 mOm and most preferred value of about 300 mOsm. Useful osmotic adjusting agents for an LMBW include, but are not limited to, potassium or sodium chloride, trehalose, sucrose, sorbitol, glycerol, mannitol, polyethylene glycols, propylene glycol, albumin, amino acids and mixtures thereof.

As used herein, the term "one-phase" describes a liquid which is substantially free of solid particles, oil droplets, or other detectable aggregates or super molecular structures in the nanometer (>5 nm and ≤1000 nm), micron or micrometer (>1 micron and ≤1 millimeter) or greater (>1 millimeter) size range. Any object in water of size less 5 nm falls in the size range of single or un-aggregated molecules, therefore is regarded as a true solution or one-phase solution.

As used herein, "pH" is a measure of the acidity or basicity of an aqueous solution. The pH determination of a composition of the present invention is typically performed with a pH meter consisting of a glass electrode connected to an electronic meter that measures and displays the pH readout. The pH meter is calibrated using standard pH buffers. Solutions with a pH less than 7 are said to be acidic and solutions with a pH greater than 7 are basic or alkaline. Pure water (i.e., pure $H_2O$) has a pH close to 7.

As used herein, a "pH buffer" means the common pH buffers used in the food, cosmetic or pharmaceutical formulations used to stabilize the pH of a solution. The preferred buffers for an LMBW include, but are not limited to, phosphate, acetate, citrate, TRIS, bicarbonate, succinate, histidine, or other amino acids.

As used herein, a "phase diagram" or "ternary phase diagram" is an equilateral triangle plot graphically depicting concentrations of the three components of interest in a combination. For the LMBW compositions of this invention, the three components are L, M and B. FIGS. 1-4 are examples of the ternary phase diagrams for L, M and B. Each axis represents the concentration (in weight percentage based on the Dry Weight) of one component. Each point in a ternary phase diagram represents a unique composition containing L, M and B. For example, the point "E" in FIG. 1 represents a combination containing 50% L, 10% M and 40% B based on the Dry Weight. The purpose of ternary phase diagram in this invention is to provide a visual & quantitative representation of the LMBW zone which was experimentally determined. With an LMBW zone displayed in a ternary phase diagram, one can readily check if a given mixture of L, M and B is within an LMBW zone, and if so, expect such mixture to form a clear and one-phase solution in water and to have the LMBW properties.

As used herein, a "preservative" is a pharmaceutical additive that can be added to a composition to inhibit bacterial and fungal growth. The antimicrobial preservatives useful in an LMBW include, but are not limited to, cresols, phenol, benzyl alcohol, ethanol, chlorobutanol, parabens, imidura, benzylkonium chloride, EDTA or its salt, or a combination thereof.

As used herein, the term "Solid LMBW" refers to a LMBW composition that exists in a solid form. Typically, a Solid LMBW contains a low water with a Water to Dry Weight ratio of less than 0.1/1 and is substantially from of alcohol. A Solid LMBW is an amorphous transparent glass-like solid having a different physical structure than its starting components (L, M, and B) if they are directly mixed together ("physical mixture") (Example 28). A Solid LMBW can be prepared by making a LMBW solution with water and/or alcohol first and then removing the water and alcohol by vacuum drying or other drying methods to reach the final water content, i.e. Water to Dry Weight ratio of less than 0.1/1. A Solid LMBW can be used to solubilize a drug and allow for incorporation into a solid dosage form such as tablet or capsule. Upon mixing with water, A Solid LMBW can be readily converted into a regular LMBW solution having the same LMBW properties.

As used herein, the term "solubility" means that a solute (such as a drug) has reached its maximum concentration in a solvent.

As used herein, the term "solubilizer" or "solubility enhancer" refers to an excipient or a combination of excipients that is used to increase the solubility of a compound of interest in water. The compound of interest may include, but not limited to a drug, a cosmetic agent, a nutritional supplement, an endogenous body component such as cholesterol, and mixture thereof.

As used herein, the term "substantially free" means containing less than 1% of the total weight of the composition of interest.

As used herein, "solution" refers to a one-phase liquid.

As used herein, the term "Universal Solubilizer" refers to a solubilizer that is capable of increasing the solubility for a compound of interest regardless of its structure, MW or physicochemical properties. More specifically, the term "Universal Solubilizer" refers to a solubilizer that is capable of increasing the solubility to ≥1 mg/mL of an inorganic element, small or non-polymeric organic molecule, peptide, or protein in water. The ≥1 mg/mL concentration is regarded as a useful concentration for pharmaceutical applications for most drugs.

As used herein, "USP" means the current edition of the United States Pharmacopeia.

As used herein and unless otherwise stated, the term "%" means the weight by weight percentage, % wt or % w/w.

As used herein, the term "Water to Dry Weight ratio" or "Water/LBM" refers to the weight ratio (w/w) of water to Dry Weight in an LMBW or a L, M and B composition of interest. For example, for a composition containing 61 g L, 21 g M, 18 g B and 150 g water, the Dry Weight is 100 g (=61 g+21 g+18 g) and the Water to Dry Weight ratio or Water/LBM ratio is 150/100 or 1.5/1.

II. DESCRIPTION OF EMBODIMENTS

It is widely known that lecithin is a useful solubilizer for insoluble drugs. In pharmaceutical formulation practice, lecithin has been used to form emulsion, liposome, mixed micelle and nanoparticle formulations. The most commonly used lecithin in drug formulations are mixtures of phospholipids derived from a natural source, typically soy beans or egg yolk. The soy or egg lecithin itself is insoluble in water. In water, lecithin generally forms a two-phase system such as an emulsion (with oil), liposome, mixed micelle (with a soluble surfactant), or nanoparticle suspension.

Lecithin can form oil-in-water or water-in-oil emulsions. Injectable emulsion compositions are generally oil-in-water type consisting of 3 members consisting of lecithin, oil and water (which is unlike an LMBW having four components L, M, B and W). Emulsions are two-phase systems consisting of an aqueous phase and oil droplets with size generally about 50-5000 nm. An injectable emulsion is white and opaque with T800 generally less than 50%. In contrast, an LMBW is clear with T800 generally exceeding 90% (Example 16). In addition, an LMBW is a one-phase solution without any oil droplet of size greater than 5 nm (Example 16) and can dissolve significantly more of an insoluble drug than an emulsion composition having the same lecithin concentration (Example 2).

Lecithin can also form liposomes in water. Liposomes are nanometer- and micrometer-sized solid particles or vesicles having a bilayer membrane formed by the lecithin phospholipid molecules. The bilayer membranes are the characteristic structural feature of liposomes. A liposome particle can range in the size from 20 nm to 40 μm in diameter. A water composition containing liposomes is clearly a 2-phase system or a suspension, whereas an LMBW is a one-phase solution without any solid particles of size greater than 5 nm (Example 16).

Lecithin can't form a clear solution or dispersion in water because it is insoluble in water. It, however, can form mixed micelles in water when combined with a water-soluble surfactant such as a bile salt. Micelles is a distinct and separate phase in water. The particle size of the lecithin-bile salt mixed micelles has been reported to be about 8 nm or greater in diameter as measured by various analytical techniques including laser light scattering (J. Wylie Nichols and Justyna Ozarowski, "Sizing of lecithin-bile salt mixed micelles by size-exclusion high-performance liquid chromatography" Biochemistry 1990, 29, 4600-4606), or an average size from 5 nm to 14 nm depending upon the bile salt concentration as confirmed by another group of researchers (Biochimica et Biophysica Acta 1808 (2011) 140-153).

In comparison, an LMBW does not contain any particles of greater than 5 nm (Ex 16). Mixed micelle compositions are ternary (3 members) mixtures consisting of lecithin, bile acid and water, whereas an LMBW is a quaternary (4 members) mixture consisting of four components: lecithin, bile acid, MCT and water. In addition, an LMBW can dissolve significantly more quantities of an insoluble drug than a mixed micelle composition having the same bile salt and lecithin concentrations (Example 2).

Lecithin has also been used to form suspensions in water where the lecithin phospholipids are homogenized in water to form small phospholipid particles (U.S. Pat. No. 5,785, 976A). In some cases, these suspended lecithin particles are also referred to as solid lipid particles of size about 20-500 nm A suspension is a 2-phase liquid.

All these lecithin-based compositions (emulsions, liposomes, mixed micelles, solid lipid particles) share the common structural feature of having two or more phases, and these two-phase systems are not self-forming and require high energy input for their formation. Therefore, they are physically unstable and would degrade (particle aggregation, phase separation) over time, which makes them less desirable for drug formulations.

Lecithin can be dissolved in oils, such as a vegetable oil, or alcohol to form a clear and one-phase solution. However, such an oil or alcohol solution of lecithin will precipitate or turn into a cream/paste-like mass immediately upon dilution with water, rendering it unsafe for intravenous injection. In contrast, an LMBW is an aqueous solution and remains as a clear and one-phase solution upon dilution with water.

The above lecithin-based but non-LMBW formulations have limited solubility enhancement potential (Example 2). For many insoluble drugs, such formulations are not pharmaceutically useful because they cannot dissolve enough drug to meet the therapeutic dose requirement.

In summary, none of these commonly employed lecithin-based drug formulations share the same structural features and physical properties as an LMBW, and an LMBW is generally superior to other lecithin-based formulations as a solubilizer.

As will be shown in the Examples below, LMBW formulations have the physical and biological properties that are very desirable for therapeutic applications, especially for formulating insoluble drug compounds. These LMBW properties are:
1. being a clear and one-phase solution,
2. can be further diluted in water or in an IV infusion fluid without any precipitation or phase separation (i.e., remains as one-phase solution after being diluted with water),
3. capable of dissolving insoluble drugs of widely different structures, i.e. a Universal Solubilizer,
4. forms spontaneously or is self-forming in water (i.e., does not require high-shear/high-pressure homogenization for its preparation), and
5. is safe for injection into human or animals, or injectable.

To find all possible mixtures or compositions of L, M, B that can form an LMBW, the inventors of this application have systematically prepared numerous compositions containing L, M, and B in water and examined each composition prepared by using visual, microscopic and/or dynamic light scattering spectrometry method to determine whether the composition was a clear and one-phase solution. Once confirmed to be clear and one-phase, the composition was further diluted in water and examined again for clarity and phase separation. If the composition remained clear and one-phase, it was marked as an LMBW with an open circle on a ternary phase diagram (Example 1).

Each prepared and tested composition is quantitatively represented by the concentrations of L, M and B (in weight percent concentration based on Dry Weight) and is depicted graphically by an open or black circle in a ternary phase diagram (see FIGS. 1-4). All compositions in a ternary phase diagram were prepared at a fixed Water to Dry Weight ratio and optionally a fixed Alcohol to Dry Weight ratio. For FIG. 4, no alcohol was added in any composition (i.e., Alcohol to Dry Weight ratio=0/1).

The open circles represent compositions that produced clear and one-phase solutions at the fixed water and alcohol levels and remained clear and one-phase after further dilution in water, whereas the black circles represent compositions that were not clear or failed to exist as a single phase.

Special efforts were made to prepare, test and ascertain the open circles that are graphically very close to the black circles. Once confirmed, these open circles were labeled as "Border points". By connecting the Border points to form an enclosed section, an LMBW zone is graphically defined or "mapped out" in the ternary phase diagram (see shaded areas in FIGS. 1-5).

In each LMBW zone shown in FIGS. 1-4, the water content or the Water to Dry Weight ratio was fixed at 1.5/1. For each LMBW zone, the water content may increase freely upward, because any composition in the LMBW zone can be diluted with water without losing the LMBW property. Similarly, an LMBW composition may be diluted with an IV infusion fluid such as Normal Saline or 5% dextrose solution to a high extent (e.g. 10× or 100×) without precipitation or phase separation (Example 11). A diluted LMBW (by water or an IV infusion fluid) would retain the LMBW properties.

It was also discovered by the inventors of this invention that an LMBW requires a minimum amount of water to form. The minimum amount of water was determined to be about 0.1/1 (in Water/Dry Weight ratio). Once the water content was reduced to below 0.1/1, an LMBW would turn into a solid (Example 14 & 18).

Alcohol can be added to an LMBW as an optional excipient. The primary purpose of adding alcohol is to further increase the solubility of an insoluble drug in the LMBW. Moreover, alcohol can reduce the viscosity of an LMBW, making it easier to inject or transfer. Some alcohols such as benzyl alcohol can also function as a preservative which will allow an LMBW formulation to be suitable for multiple injections or dosing.

As the alcohol concentration increases, the area of the LMBW zone will also increase. For example, the area of the LMBW zone in FIG. 1 (with 0.49/1 in Alcohol to Dry Weight ratio) is greater than that in FIG. 3 (with 0.24/1 in Alcohol to Dry Weight ratio). However, it appeared that the LMBW area would reach a maximum at 0.49/1 (in Alcohol to Dry Weight ratio), as further increase in alcohol concentration from 0.36/1 (FIG. 2) to 0.49/1 (FIG. 1) did not result in a significant increase in the LMBW zone. Therefore, it is believed that the LMBW zone shown in FIG. 1 (or described in Claim 1 & 2) represents the greatest LMBW zone possible.

In one aspect, the greatest LMBW zone contains from about 6% to about 72.5% L, such as 6%, 10%, 15%, 20%, 25%, 20%, 35%, 40%, 45%, 50%, 55%, 60%, 65%, 70% or about 72.5% L; between 0% and about 32.5% M, such as 0.1%, 2%, 5%, 10%, 15%, 20%, 25%, 30% or about 32.5% M, and from about 11.5% to about 94% B, such as 11.5%, 15%, 20%, 25%, 30%, 35%, 40%, 45%, 50%, 55%, 60%, 65%, 70%, 75%, 80%, 85%, 90% or about 94% B in water.

In another aspect, the greatest LMBW zone is within (but not including Border points where the value is 0) the section enclosed by the following Border points:

| Border points | Concentration (% w/w based on the Dry Weight) | | |
| --- | --- | --- | --- |
| (as in FIG. 1) | Lecithin | MCT | Bile salt |
| A | 72.5 | 0 | 27.5 |
| B | 61 | 27 | 12 |
| C | 56 | 32.5 | 11.5 |
| D | 52 | 32.5 | 15.5 |
| E | 50 | 10 | 40 |
| F | 6 | 0 | 94 |

In FIG. 1, each side or axis denotes the concentration of the labeled component. The arrow under each axis label points to the angle which represents 100% w/w of the labeled component. For example, the top angle represents a composition that is 100% w/w in Lecithin and 0% in Bile salt. Similarly, the lower and right angle represents 100% w/w in Bile salt and 0% w/w in MCT and the lower left angle 100% w/w MCT and 0% w/w Lecithin. Any point on an axis is binary mixture such as the Border points A & F. Each point inside the triangle represents a ternary mixture. For example, Border point B contains 61% w/w L, 27% M and 12% B. The purpose of the ternary phase diagram is to provide a visual and quantitative presentation of the LMBW zone. An LMBW zone is the grey area enclosed by the Border points (open circles). The lines connecting the Border points form the borders that separate the LMBW zone from the non-LMBW zones, which are mapped out by the solid circles. Each open circle or solid circle composition was experimentally prepared and tested to determine whether it is a clear and one-phase solution. It is worthwhile to note that any composition that falls on the A-F line cannot be regarded as an LMBW since MCT is absent.

With an LMBW zone displayed in a ternary phase diagram, one can readily check if a given mixture of L, M and B can form an LMBW, and if so, expect such mixture to have the LMBW properties. For each ternary phase diagram (FIGS. 1-4), the water concentration is also provided in the Water to Dry Weight ratio or Water/LMB (w/w), and similarly, the alcohol concentration is expressed in the Alcohol to Dry Weight ratio or Alcohol/LMB ratio (w/w).

To an LMBW composition derived from the greatest LMBW zone, more alcohol may be added while maintaining the solution clear and one-phase. However, for safety considerations, the FDA has placed an upper limit for alcohol content at about 20% of the final weight of the formulation for drugs that are injectable directly into blood vessels (e.g. intravenously) or into a soft tissue (e.g. intramuscularly). Therefore, the preferred alcohol concentration in an LMBW is about up to 20% (based on the final weight of the formulation at the time of the injection). Nevertheless, more alcohol can still be added if the formulation is diluted before injection.

It is worthwhile to note that (1) the addition of alcohol is optional for an LMBW composition, and (2) an alcohol-containing LMBW composition will retain all LMBW properties.

Figure 5:
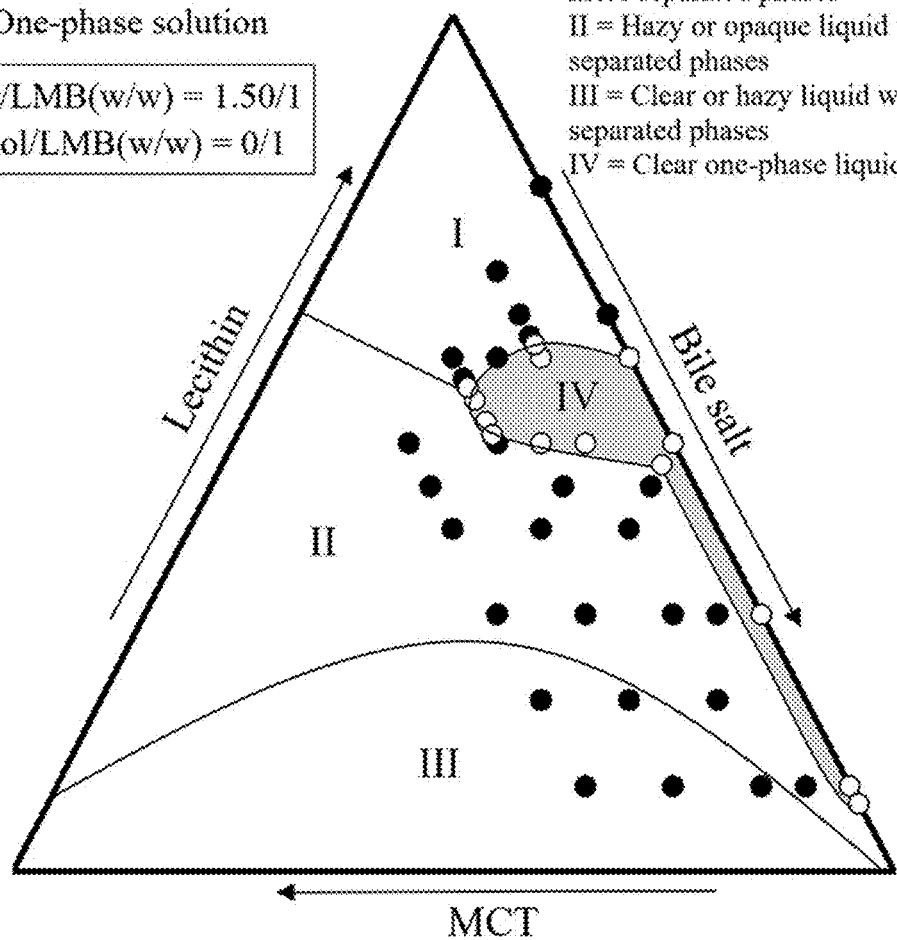
FIG. 5 illustrates a ternary phase diagram in an equilateral triangle plot graphically depicting concentrations (in % w/w based on the Dry Weight or combined weight of L, M and B) of the three components (L, M and B) in combinations with a fixed amount of water according to the present invention.

FIG. 5 illustrates a ternary phase diagram for L, M and B without alcohol or Alcohol/LMB (w/w)=0/1, wherein only within the LMBW zone (Zone IV), a composition is a clear and one-phase solution. In any other region (I, II or III), a composition is not clear or has more than one phases.

It was also observed that any composition of L, M and B outside the LMBW zone would form multi-phase liquids or semi-solids in water, namely emulsions, suspensions, gels, etc. (FIG. 5).

An LMBW can form spontaneously in water or is self-forming. A clear and one-phase composition within an LMBW zone can be easily formed using a low-energy mixer to disperse and dissolve L, M and B in water. No special high temperature, high speed, high pressure, extrusion, microfluidization or high energy homogenization is required. This characteristic of LMBWs contrasts with other lecithin-based compositions such as emulsions, suspensions, or liposomes, all of which require high-energy homogenization methods for their preparation.

Similarly, to dilute an LMBW with water or an IV infusion fluid, only gentle mixing is needed. This readily water-dilute-able feature of an LMBW is particularly useful for IV infusion, wherein the LMBW is provided as a "concentrate" drug formulation and is diluted with water or an IV infusion fluid before administration.

The self-forming nature (no need for high-energy homogenization) of an LMBW also suggests that it is a thermodynamically favorable system and is physically stable. Unlike other lecithin-based formulations, an LMBW will remain as a clear and one-phase solution and will not form precipitates or undergo aggregation or phase separation over time (Example 12). In contrast, an emulsion, liposome, micelle or suspension composition is NOT a thermodynamically favorable system; over time, the components in these systems will aggregate and the system will separate into distinct phases. For example, over time, an emulsion will "cream out" into aggregated and separated phases.

The fact that an LMBW composition is a clear and one-phase solution is highly desirable to the patient, nurse, or physician. The solution transparency allows the user to visually examine the drug preparation before use to ensure there are no solid particles, microbial growth or other aberrant content. This contrasts with most other lecithin-, MCT- or bile salt-based compositions described in the prior art, which are either intrinsically opaque or cloudy (e.g., liposomes, emulsions), or turn milky or precipitate after dilution in water (e.g., solvent-based or micelle solutions).

An LMBW is a ready-to-use formulation that can be injected directly without prior dilution. Such a ready-to-use formulation is desired because it eliminates certain steps of preparation or dilution that can be tedious or prone to medical error. A ready-to-use LMBW formulation is of importance for rescue drugs that require immediate administration under emergency circumstances, and where there is little or no time for dilution.

Within the LMBW zone, various compositions containing different drugs have been selected, prepared and demonstrated to have the desired LMBW properties (see Examples 4-29).

For drugs that are unstable in water, an anhydrous (water-free) LMBW composition may be used. An anhydrous LMBW is an LMBW devoid of water to a water content below 0.1/1 in weight ratio of water to the Dry Weight. Upon mixing with water, the anhydrous LMBW can form a LMBW solution having the same LMBW properties.

An anhydrous LMBW may be produced by removing water using lyophilization or other drying methods (e.g., vacuum drying). Like a lyophilized or other dried drug formulation, an anhydrous LMBW provides a new option to formulate water-sensitive drugs. An anhydrous LMBW may exist as a solution with alcohol as the liquid vehicle, an opaque solid or a transparent glass-like solid (see Solid LMBW).

Alternatively, an anhydrous LMBW may be produced by direct mixing L, M and B with each at a concentration within an LMBW zone.

In an aspect, an LMBW may be provided without a drug. A drug is not an essential component of an LMBW. A drug-free LMBW vehicle (Part 1) can be prepared, then subsequently mixed with a drug (Part 2) prior to administration. This two-part system may be desirable for drugs that do not have long-term stability after the two parts are combined.

In an aspect, an LMBW may be provided with a drug in it. To incorporate a drug into an LMBW vehicle, the drug substance is added to an LMBW and then mixed until the drug is dissolved. The drug substance may be added to and dissolved in a pre-made LMBW vehicle, or it may be added at any step during the preparation of an LMBW (Examples 2, 3, 4 and 15).

In an aspect, an LMBW composition is a one-phase liquid and is free of any oil droplets, solid particles, aggregates or super molecular structure that are detectable with the naked eye or by using certain particle-detecting analytical instruments such as a microscope or a DLS spectrometer (Example 13 & Example 16). A one-phase composition such as an LMBW is preferred over multi-phase compositions because of the LMBW's transparency, physical stability, and simple manufacturing process.

In an aspect, an LMBW composition is a one-phase liquid and is free of DLS detectable oil droplets, solid particles, aggregates or super molecular structure of size greater than 5 nm, preferably greater than 2 nm or more preferably greater than 1 nm in diameter.

In an aspect, an LMBW composition is clear with T800 greater than 70%, preferably greater than 80% or more preferably 90%.

In another aspect, an LMBW has a viscosity at between about 1 and 10,000 centipoises or cP, preferably, 10-1,000 cP or more preferably 10-100 cP.

In an aspect, an LMBW can be passed through a 0.2-micron filter membrane. This allows the sterilization of the LMBD composition by simple filtration (Example 3).

In an aspect, an LMBW vehicle (without drug) can also be sterilized by heat-sterilization methods such as autoclaving. If a drug is not heat sensitive, then the LMBW containing the drug may also be suitable for heat sterilization.

In an aspect, an LMBW further contains an excipient such as an acid, antioxidant, base, pH buffer, bulking agent, metal chelator, preservative, viscosity enhancer, osmotic pressure adjuster, or inert gas e.g., nitrogen etc.

In an aspect, all components in an LMBW are regarded safe for injection or injectable. The key components L, M and B have been previously approved by the FDA for use in injectable drugs. Phosphatidylcholines, bile salts and triglycerides are endogenous to the human body as they are found in the human blood. Experimentally, LMBW compositions have been shown to be safe in both animals and humans following injection into soft tissue (via subcutaneous injections) and into blood vessels (via intravenous injections) (Examples, 5, 6 & 15).

An LMBW containing an insoluble psychoactive drug diazepam was tested in human for safety and pharmacokinetic profiles following a subcutaneous injection. This was a Phase 1 trial under an IND approved by the FDA. The LMBW formulation was found to be well-tolerated in human subjects without any significant adverse event observed. The same formulation was also tested in rodents and dogs and was found to be safe following subcutaneous injection (Example 15). In an aspect, an LMBW composition containing diazepam is administered by intravenous, intramuscular, subcutaneous injection, by oral ingestion, and/or rectal insertion. In an aspect, an LMBW composition containing diazepam is used for anxiety, alcohol withdrawal syndrome, benzodiazepine withdrawal syndrome, muscle spasms, seizures, trouble sleeping, restless legs syndrome or in emergency situations to stop cluster seizures. In an aspect, an LMBW composition contains 0.1-3 mg/mL diazepam such as 0.1, 0.5, 1, 1.5, 1.6, 1.7, 1.8, 1.9, 2, 2.1, 2.2, 2,4, 2.5 and/or 3 mg/mL. In an aspect, an LMBW composition contains a diazepam dose of 1-20 mg such as 1, 2, 3, 4, 5, 6, 7, 8, 9, 10, 11, 12, 13, 14, 15, 16, 17, 18, 19, 20 mg. In an aspect, an LMBW composition containing a diazepam is dosed at 0.1-5 mL such as 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3, 4, or 5 mL. In an aspect, an LMBW composition containing diazepam is dosed at the onset of a seizure, or at a frequency of every 1-24 hours.

Surprisingly, an LMBW composition appeared to have reduced the hemolytic or irritation potential of the bile salt it contains (Example 17). Bile salts are known to cause hemolysis and tissue irritation (Cell Mol Biol Lett. 2001; 6(4):881-95), and such toxicities are commonly manifested as injection-site reactions. For example, BELKYRA™ injection, which contains the bile salt deoxycholic acid as the active ingredient, is associated with severe injection-site reaction. The package inserts for BELKYRA™ injection reveals that the drug causes injection-site bleeding/hematoma in 61% of patients administered the drug subcutaneously. However, such injection-site toxicity was not observed in either animals or humans for an LMBW following subcutaneous injections (Example 15), indicating that the combination of bile salt with M and L in an LMBW composition apparently has reduced or eliminated the hemolysis/tissue irritation problem associated with the bile salt.

An LMBW composition is unique because (1) it can only be made with L, M, and B within the LMBW zone, and (2) none of these 3 components can be readily substituted with other ingredients of similar structure or physical properties. For example, lecithin is a lipophilic surfactant, but other lipophilic surfactants such as Span 40 cannot replace lecithin to form an LMBW. Even different lecithin behaved differently in an LMBW, the preferred lecithin for an LMBW is soy lecithin having phosphatidylcholine at 75% or greater based on the lecithin weight (Example 7). Similarly, the M in an LMBW cannot be substituted with a longer chain triglyceride (LCT) such as sesame oil (Example 8), and the B in an LMBW cannot be substituted by another water-soluble surfactant such as the sodium salt of fatty acids.

To further demonstrate the uniqueness and utility of LMBW compositions, the inventors have prepared and tested numerous other possible binary (two components) or ternary (three component) combinations using the same L, M, B, alcohol and water components and found that none of the binary or ternary compositions had the same LMBW properties (Example 2). Any of these non-LMBW compositions would have one or more of the following drawbacks, including:
 a. Not clear or transparent;
 b. Not a one-phase solution;
 c. Becomes cloudy or precipitates when diluted with water;
 d. Requires high shear or high energy homogenization to form;
 e. Does not dissolve an insoluble drug to the same extent as an LMBW; and
 f. Is hemolytic or irritating to tissue at the injection site (Example 17).

Surprisingly, the components (L, M, B) synergistically provide much greater solubility for an insoluble drug (e.g., voriconazole) when they are together in an LMBW composition than singly or in combinations other than an LMBW (Example 2).

In an aspect, for the same amount of lecithin in the formulation, an LMBW can dissolve a greater amount of an insoluble drug compared to other lecithin-based solubilizing formulations such as liposomes, emulsions, alcohol solutions or mixed micelles.

In an aspect, for the same amount of MCT in the formulation, an LMBW can dissolve a greater amount of an insoluble drug than other MCT-based solubilizing formulations such as emulsions.

In an aspect, for the same amount of bile salt in the formulation, an LMBW can dissolve a greater amount of an insoluble drug than other bile salt-based solubilizing formulations such as micelles or mixed micelle solutions.

In an aspect, for the same amount of alcohol in the formulation, an LMBW can dissolve a greater amount of an insoluble drug than other commonly used alcohol-based solubilizing formulations such as alcohol-water cosolvent.

In an aspect, L, M, B, and W when combined in an LMBW formulation provide solubility enhancement for an insoluble drug that is usually much greater than the sum of solubilities achieved by each component separately, and greater than when the components are combined in a form of liposomes, emulsions, micelles, suspensions, mixed micelles or alcohol solutions (Example 2). In an aspect, L, M and B in an LMBW can synergistically enhance solubility of an insoluble drug in water.

In an aspect, an LMBW can dissolve a soluble drug to obtain a clear solution formulation. Because of the presence of L, M and B, an LMBW may act as a fast- or slow-releasing formulation once injected into a soft tissue.

Also, an LMBW compares favorably to many other known drug solubilizers. For example, an LMBW can dissolve the highly insoluble drug voriconazole to the same drug concentration as in the marketed drug product ("VFEND® I.V.") which uses a cyclodextrin as a solubilizer to dissolve voriconazole. Surprisingly, the LMBW formulation for voriconazole exhibited the same pharmacokinetic profiles (FIG. 6) as the VFEND® I.V. formulation yet is free of the kidney toxicity commonly associated with cyclodextrin-based formulations (Example 6). In an aspect, an LMBW composition containing voriconazole is administered by intravenous, intramuscular, subcutaneous injection, oral ingestion, installation into the eyes or ears, and/or rectal insertion. In an aspect, an LMBW composition containing voriconazole is used as an antifungal medication used to treat a number of fungal infections, including but not limited to aspergillosis, candidiasis, coccidioidomycosis, histoplasmosis, penicilliosis, and infections by *Scedosporium* or *Fusarium*. In an aspect, an LMBW composition contains 1-60 mg/mL voriconazole such as 1, 2, 3, 4, 5, 6, 7, 8, 9, 10, 11, 12, 13, 14, 15, 16, 17, 18, 19, 20, 25, 30, 35, 40, 45, 50, 55, or 60 mg/mL. In an aspect, an LMBW composition contains a voriconazole in a drug to Dry weight ratio between 0.027/1 and 0.16/1. In an aspect, an LMBW composition contains a voriconazole dose of 1-200 mg such as 1, 2, 3, 4, 5, 6, 7, 8, 9, 10, 11, 12, 13, 14, 15, 16, 17, 18, 19, 20, 50, 100, or 200 mg. In an aspect, an LMBW composition containing a voriconazole is dosed at 0.1-20 mL such as 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3, 4, 5, 10, or 20 mL. In another aspect, an LMBW composition containing voriconazole is lyophilized or substantially free of water. In another aspect, an LMBW composition containing voriconazole is dosed at a frequency of every 6-24 hours. In yet another aspect, an LMBW composition containing voriconazole is bioequivalent to the VFEND® I.V. formulation.

In an aspect, a drug in an LMBW formulation is safer than a cyclodextrin-based formulation of the same drug.

In an aspect, an LMBW is safe for repeated daily intravenous injection into beagle dogs at 4-6 mL per day.

In an aspect, an LMBW is pharmacokinetically equivalent to or bioequivalent to a cyclodextrin formulation containing the same drug.

In an aspect, an LMBW can provide a greater solubility for an insoluble drug than a cyclodextrin formulation (Example 25).

In an aspect, an LMBW can substitute the cyclodextrin as a solubilizer for the drug products that are currently formulated with cyclodextrins. The cyclodextrin-solubilized drugs include but are not limited to cannabidiol, PGE2, PGE1, opalmon, piroxicam, benexate HCl, iodine, dexamethasone, nitroglycerin, cefotiam-hexetil, cephalosporin, tiaprofenic acid, diphenhydramin and chlortheophyllin, chlordiazepoxide, hydrocortisone, itraconazole, cisapride, nimesulide, alprostadil, nicotine, chloramphenicol, diclofenac sodium, estradiol, indomethacin, omeprazol, posaconazole, tetrahydrocannabinol, voriconazole, ziprasidone mesylate, dextromethorphan, cetirzine, mitomycin, meloxicam, and aripiprazole.

In an aspect, an LMBW can dissolve each of the following insoluble drugs, diagnostic agents or nutritional supplements to a level that is significantly higher than its intrinsic solubility in water: amiodarone, amphotericin, aprepitant, bacitracin, camptothecin, casein, clarithromycin, cyclosporine, diazepam, docetaxel, ibuprofen, celecoxib, itraconazole, irinotecan, iodine, levodopa, paclitaxel, phytonadione, posaconazole, prednisolone acetate, progesterone, propofol, resveratrol, tyrosine, oriconazole, or a salt or a combination thereof (Example 4).

In Example 4, an LMBW composition was shown to increase solubility of drug molecules over a wide range of molecular weights, chemical structures, physicochemical properties and therapeutic uses. Based on these observations, it is reasonable to regard an LMBW composition as a "Universal Solubilizer" for its broad utility in solubilizing insoluble drugs.

In an aspect, an LMBW is substantially-free of drug i.e., the LMBW contains 0% drug. In other aspects, the LMBW composition contains 0-25% w/w drug such as 0, 1, 2, 3, 4, 5, 6, 7, 8, 9, 10, 11, 12, 13, 14, 15, 16, 17, 18, 19, 20, 21, 22, 23, 24, and/or 25% w/w drug. In certain aspects, the amount of drug or active agent is about 0.1% to about 5%, or about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, and/or 5% w/w, all based on the final weight of the composition. In other aspects, the LMBW composition contains a drug at 0/1-0.5/1 in drug weight ratio to the Dry weight, such as 0/1, 0.1/1, 0.2/1, 0.3/1, 0.4/1, 0.5/1, 0.6/1, 0.7/1, 0.8/1, 0.9/1 and/or 1/1. In another aspects, a LMBW composition contains a drug dose ranging from 0.001 mg to 100 g. In another aspects, a drug-containing LMBW composition is provided in a volume ranging from 0.001 mL to 10 L. In yet another aspect, a drug-containing LMBW composition is dosed continuously, hourly, 4 times a day, 3 times a day, twice a day, once-a-day, once every 2 days, once every 3 days, once every 4 days, once every 5 days, once every 6 days, once-a-week, once-every 2 weeks, and/or monthly.

The drug solubilization potential of a cyclodextrin is limited by a drug's ability to form an inclusion complex with the cyclodextrin. The inclusion complex requires the drug molecule to have certain molecular weight, size and structure. In other words, unlike an LMBW, cyclodextrin cannot be considered a Universal Solubilizer.

In another aspect, an LMBW can also be used to dissolve and/or deliver a cosmetic, diagnostic agent or nutritional supplement. An LMBW for such purposes can be administered to a human or animal patient by injection or instillation, or by oral, topical, ophthalmic, otic, nasal, inhalation, vaginal, or rectal administration.

In one aspect, an LMBW vehicle alone that does not contain a drug could also have medical utility. For example, an LMBW may be injected into fat tissue to dissolve fats for therapeutic or cosmetic purposes like BELKYRA™ (Example 29). In addition, an LMBW solution may be used as a biocompatible cleansing liquid to clean body parts such as skin, eye, ear, nose, vagina, rectum, wound (debridement with or without enzymes), mucus, soft tissue, or hair, etc., for therapeutic, personal care or cosmetic purposes.

In an aspect, an LMBW composition can be used to dissolve and remove undesirable insoluble solid deposits in human or animal bodies such as uric acid deposits as in gout, kidney stones, cholesterol deposits in atherosclerosis or xanthelasma and the protein deposits in Alzheimer's (amyloids) (Example 29).

In an aspect, an LMBW can be injected as is or is ready-to-use. In another aspect, an LMBW is a concentrate, in yet another aspect, an LMBW is both a ready-to-use and a concentrate formulation. and in yet another aspect, an LMBW is initially provided in an anhydrous form and formed upon mixing with water.

In an aspect, the present invention provides a clear and one-phase aqueous solution composition, comprising (a) lecithin at a concentration between 6% and 72.5%, (b) MCT at a concentration between 0% and 32.5% and (c) a bile salt at a concentration between 11.5% and 94%, wherein all concentrations are in weight percentage over the Dry Weight and the solution composition further contains alcohol at a concentration of 0.49/1 or less in Alcohol to Dry Weight Ratio.

In an aspect, the present invention provides a clear and one-phase aqueous solution composition, comprising (a) lecithin at a concentration between about 8% and about 61.5%, (b) MCT at a concentration between about 0% and about 23% and (c) a bile salt at a concentration between about 22% and about 92%, wherein all concentrations are in weight percentage over the Dry Weight and the solution composition is substantially free of alcohol.

In an aspect, the present invention provides a clear and one-phase aqueous solution composition, comprising lecithin, MCT and bile salt in a composition within an LMBW zone in a ternary phase diagram having lecithin, MCT and bile salt as the three components, wherein the LMBW zone is enclosed by the following Border points:

| Labels of Border points as in FIG. 1 | Concentration (in Weight Percent over the Dry Weight) | | |
|---|---|---|---|
| | Lecithin | MCT | Bile salt |
| A | 72.5 | 0 | 27.5 |
| B | 61 | 27 | 12 |
| C | 56 | 32.5 | 11.5 |
| D | 52 | 32.5 | 15.5 |
| E | 50 | 10 | 40 |
| F | 6 | 0 | 94 |

Furthermore, the solution composition contains alcohol at a concentration of 0.49/1 or less in Alcohol to Dry Weight Ratio.

Figure 4:
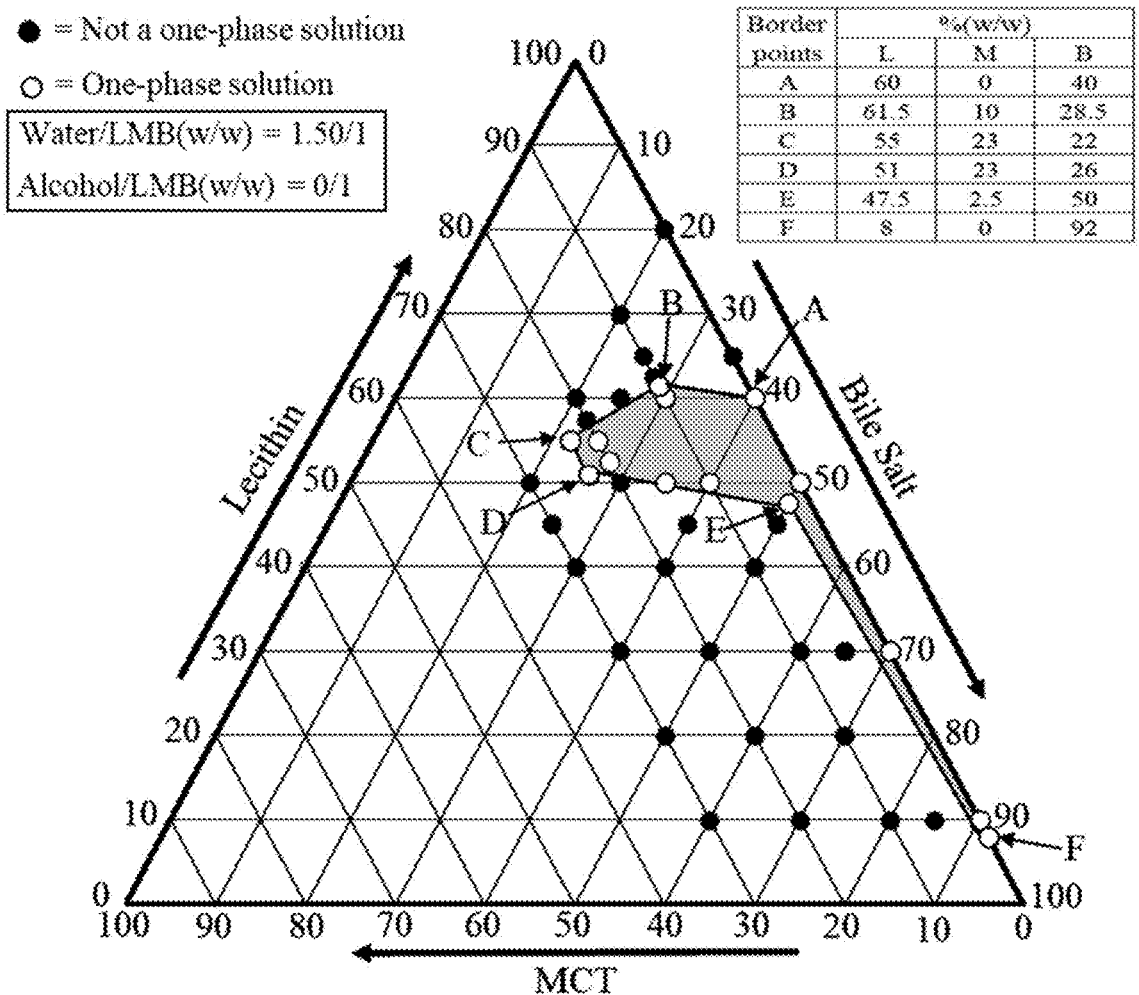
FIG. 4 illustrates a ternary phase diagram in an equilateral triangle plot graphically depicting concentrations (in % w/w based on the Dry Weight or combined weight of L, M and B) of the three components (L, M and B) in combinations with a fixed amount of water according to the present invention.

In an aspect, the present invention provides a clear and one-phase aqueous solution composition, comprising lecithin, MCT and bile salt in a composition within an LMBW zone in a ternary phase diagram having lecithin, MCT and bile salt as the three components, wherein the LMBW zone is defined by connecting the following Border points in a circle:

| Labels of Border points as in FIG. 4 | Concentration in Weight Percent over the Dry weight) | | |
|---|---|---|---|
| | Lecithin | MCT | Bile salt |
| A | 60 | 0 | 40 |
| B | 61.5 | 10 | 28.5 |
| C | 55 | 23 | 22 |
| D | 51 | 23 | 26 |
| E | 50 | 10 | 40 |
| F | 8 | 0 | 92 |

Furthermore, the solution composition is substantially free of alcohol ("alcohol-free").

In another aspect, an LMBW composition of this invention contains alcohol at a concentration between 0/1 and 0.49/1 in Alcohol to Dry Weight Ratio. At 0/1 Alcohol to Dry Weight ratio, the smallest LMBW zone was obtained (FIG. 4) and at 0.49/10/1 Alcohol to Dry Weight ratio, the largest LMBW zone was obtained (FIG. 1).

These LMBW zones are very useful in drug formulation especially for selection of a formulation vehicle to solubilize an insoluble drug. For a drug formulation that could contain some alcohol, one could select several (3 or 4) LMBW compositions at different positions within the largest LMBW zone (FIG. 1) as the formulation vehicles, then measure and compare the solubility of the insoluble drug achieved by these LMBW vehicles and select one preferred vehicle that provided the greatest solubility.

In another aspect, an LMBW composition of this invention contains alcohol at a concentration no more than 1.6/1 in Alcohol to Dry Weight Ratio. A higher alcohol concentration lead to precipitation (Example 18).

In another aspect, an LMBW composition of this invention contains alcohol at a concentration no more than 10%, 20%, 30%, 40%, 50%, 60%, or 70% of the total weight of the final formulation.

In another aspect, alcohol is selected from the group consisting of ethanol, benzyl alcohol, propylene glycol, polyethylene glycol of a low molecular weight (100-5,000) or a combination thereof. The preferred alcohol for an LMBW is ethanol, benzyl alcohol, propylene glycol or a combination thereof.

For a drug formulation in which an alcohol is not desired, a similar selection process may be applied using the LMBW zone in FIG. 4, where one could select several (3 or 4) LMBW compositions at different positions within the LMBW zone as the formulation vehicles, then measure and compare the solubility of the insoluble drug achieved by these vehicles, and select one preferred vehicle that provided the greatest solubility.

In another aspect, an LMBW composition of this invention has a pH between about 3 and about 10. In a preferred aspect, the composition of this invention has a pH between about 4 and about 9. In a more preferred aspect, the composition of this invention has a pH between about 4 and about 8. In another aspect, an LMBW composition of this invention has a pH at 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.0, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8.8, 8.1, 8.2, 8.3, 8.4, 8.5, 8.6, 8.7, 8.8, 8.9, or 9.0.

In another aspect, the composition of an LMBW has an acid and/or base for pH adjustment. The preferred acid is hydrochloric acid and the preferred base is sodium hydroxide.

In yet another aspect, an LMBW contains a preservative. The preferred preservative is benzalkonium chloride, cresol, metacresol (m-cresol), phenol, parabens, benzyl alcohol, EDTA or a mixture thereof. The concentrations that may be used are about 0.01% to 1% for benzalkonium chloride, about 0.08 to 0.315% for cresol/metacresol, 0.06 to 1.3% for phenol, about 0.01 to 1.5% for a paraben, about 0.05 to 10% for benzyl alcohol, about 0.005 to 0.2% for EDTA disodium, and about 0.005 to 0.34% for EDTA calcium disodium. All percentages are on a weight of the individual component to the weight of the composition basis.

In one aspect, An LMBW further contains an antioxidant. The useful antioxidants may include but are not limited to an inert gas, methionine, cysteine, dextrose, fructose, lactose, and a metal chelator such as a salt of edetate (EDTA), or combination thereof. A preferred antioxidant is a combination of methionine and EDTA. The concentration of each antioxidant may be determined based on its stabilizing effect on any component in the composition of this invention and its safety to the patient. A normal range of concentration for each antioxidant can be found in the FDA's Inactive Ingredient List. For example, the methionine concentration range useful for injectable formulations is 0.01% to 49.2% by weight of the composition.

In yet another aspect, an LMBW comprises a bulking agent. The preferred bulking agent is mannitol, sucrose, lactose, trehalose, maltose, starch or a mixture thereof. The concentrations may be used are about 1% to 20% by weight of the composition.

In another aspect, an LMBW provides a method to prepare a drug-free LMBW composition, comprising: (1) combining lecithin, MCT and bile salt and water, and (2) mixing to dissolve lecithin, MCT and bile salt in water to form a clear and one-phase liquid.

In another aspect, the present invention provides a method to prepare a drug-containing LMBW composition, comprising: (1) combining lecithin, MCT and bile salt and water, and (2) mixing to dissolve lecithin, MCT and bile salt in water to form a clear and one-phase liquid, where the drug can be added to LMBW composition and mixed to dissolve at any step.

In another aspect, the present invention provides a method to prepare a drug-containing LMBW composition, comprising: (1) combining lecithin, MCT and bile salt and water, and (2) mixing to dissolve lecithin, MCT and bile salt in water to form a clear and one-phase liquid, where the drug or a pharmaceutical excipient(s) can be added to the LMBW composition and mixed to dissolve at any step. The pharmaceutical excipient(s) may be alcohol, acid, base, pH buffer, antioxidant, bulking agent, viscosity enhancing agent, osmotic adjusting agent, preservative or a combination thereof.

In another aspect, the present invention provides a method to prepare a drug-containing LMBW composition, comprising: (1) combining the drug, lecithin, MCT and bile salt and water, and (2) mixing to dissolve lecithin, MCT and bile salt in water to form a clear and one-phase liquid, where the pH of the liquid is adjusted with an acid or base at any step.

In another aspect, the present invention provides a method to prepare a drug-containing LMBW composition, comprising: (1) combining the drug, lecithin, MCT and bile salt and water, and (2) mixing to dissolve lecithin, MCT and bile salt in water to form a clear and one-phase liquid, which is subsequently filtered through a membrane.

The solution formulation of the present invention can be administered as is (undiluted) or diluted with water prior to administration. Dilutions can also be made using IV infusion fluids. The route of administration may include, but is not limited to, injection and inhalation, or by oral, otic, nasal, topical, ophthalmic, vaginal, and rectum administration. The solution formulation of the present invention can be delivered using devices including, but not limited to, needles/syringes, infusion sets, infusion pump, catheters, applicators, bottles, sprayers, inhalation devices, and wound dressing.

In one aspect, the solution composition of this invention is autoclaved.

In one aspect, the solution composition of this invention is stable for 6 months or longer.

In one aspect, the composition of this invention has an osmotic pressure of about 100 to 600 mOsmol/L.

In one aspect, the composition of this invention is used to deliver a drug into a human or animal patient.

In one aspect, the composition of this invention is used for treatment, prevention or diagnosis of a disease in a human or in an animal.

In one aspect, the composition of this invention is used in cosmetic or nutritional supplements formulations.

The present invention will be further understood by reference to the following non-limiting examples.

III. EXAMPLES

Example 1

The aim of this study was to map out the LMBW zone in a ternary phase diagram consisting of lecithin, MCT and a bile salt. Phospholipon 90G was used as lecithin, Miglyol 812 as the MCT and sodium glycocholate as the bile salt. For each composition of interest, the calculated amounts of lecithin, MCT and bile salt and water were weighed into a glass container and prepared and tested in the following steps:

A: Prepare an LMBW without Alcohol
1. Weigh out and mix all 3 components (L, M and B) with some water.
2. Adjust pH to 7.2 with HCl/NaOH.
3. Add more water to the desired Water to Dry Weight ratio.
4. Mix to dissolve L, M and B.
5. Let liquid sit at RT for 15-30 minutes to allow for possible phase separation.
6. Observe for clarity and phase separation visually and microscopically.

7. If a clear and one-phase liquid was obtained, dilute 10× and 100× with an IV infusion fluid (5% dextrose in water or D5W).
8. Repeat steps 5-6.

B. Prepare an LMBW with Alcohol

9. Obtain a sample prepared at step 4 above.
10. Add alcohol to the desired Alcohol to Dry Weight ratio.
11. Mix well.
12. Centrifuge to force any phase separation that might occur.
13. If a clear one-phase liquid remains after centrifugation, dilute 10× and 100× with an IV infusion fluid (5% dextrose in water or D5W).
14. Repeat step 12.
15. For each level of alcohol added (including no alcohol), plot all compositions prepared and tested on a ternary phase diagram (FIGS. 1-4). Denote the plot points of compositions that remain as clear and one-phase solutions by an open circle, and the compositions that are not clear or one-phase by a solid circle.
16. Select the open circles that are closest to the solid circles as the Border points.
17. Connect the Border points to encompass the largest area that does not contain any filled circles to demarcate the graph area showing the extent of potential successful LMBW formulations (the "LMBW zone").

The table below lists the Border points at four levels of alcohol content. These Border points are graphically displayed in FIGS. 1-4.

| Alcohol content (expressed in Alcohol to Dry Weight ratio) | Border points (as shown in FIGS. 1-4) | Concentration (% w/w over the Dry Weight) | | |
|---|---|---|---|---|
| | | Lecithin | MCT | Bile Salt |
| 0/1 (FIG. 4) | A | 60 | 0 | 40 |
| | B | 61.5 | 10 | 28.5 |
| | C | 55 | 23 | 22 |
| | D | 51 | 23 | 26 |
| | E | 47.5 | 2.5 | 50 |
| | F | 8 | 0 | 92 |
| 0.24/1 (FIG. 3) | A | 70 | 0 | 30 |
| | B | 59 | 20 | 21 |
| | C | 53 | 24 | 23 |
| | D | 51.5 | 20 | 29.5 |
| | E | 42.5 | 7.5 | 50 |
| | F | 6 | 0 | 94 |
| 0.36/1 (FIG. 2) | A | 72.5 | 0 | 27.5 |
| | B | 60 | 20 | 20 |
| | C | 56 | 32.5 | 11.5 |
| | D | 52 | 32.5 | 15.5 |
| | E | 50 | 10 | 40 |
| | F | 6 | 0 | 94 |
| 0.49/1 (FIG. 1) | A | 72.5 | 0 | 27.5 |
| | B | 61 | 27 | 12 |
| | C | 56 | 32.5 | 11.5 |
| | D | 52 | 32.5 | 15.5 |
| | E | 50 | 10 | 40 |
| | F | 6 | 0 | 94 |

At 0/1 Alcohol to Dry Weight ratio, the LMBW zone obtained is the smallest (FIG. 4 zone) and at 0.49/1 Alcohol to Dry Weight ratio, the LMBW zone obtained is the largest (FIG. 1 zone). For any formulation that contain an alcohol, it is reasonable to use the largest LMBW zone as the starting place to develop a formulation for an insoluble drug.

Example 2

The aim of this study was to compare the solubility enhancement for an insoluble drug by an LMBW with other mixtures of the same components, i.e., L, M, B and alcohol.

For this study, voriconazole was used as the insoluble drug. The LMBW contains soy lecithin, MCT, bile acid (as a pH-adjusted stock solution in water), and alcohols (ethyl and benzyl) in water. The other mixtures were binary or ternary combinations of these components in water with each component at the same concentration as in the LMBW.

The LMBW prepared in this study contains 49.4% L, 29.7% M and 20.9% B based on the Dry Weight, an Alcohol to Dry Weight ratio of 0.22/1 and a Water to Dry Weight ratio of 0.98/1. This composition is within the LMBW zone as in FIG. 1.

To determine solubility in each combination, voriconazole was added to each combination and mixed until it no longer would dissolve. For each mixture, the pH was adjusted to pH 4.5-5, equilibrated at room temperature, and then passed through a 0.2-micron filter. The filtrate was analyzed by HPLC for voriconazole concentration. Each HPLC-determined voriconazole concentration is noted as a "Voriconazole solubility" in the tables below.

| Component | Concentration of each component (% wt over the total weight of each composition) | | | | | | |
|---|---|---|---|---|---|---|---|
| Lecithin | 25 | 25 | | | 25 | 25 | |
| Glycocholic acid | 10.6 | | 10.6 | | 10.6 | | |
| MCT | 15 | | | 15 | | | 15 |
| Benzyl alcohol | 4.5 | | | | 4.5 | | |
| Ethanol | 6.5 | | | | 6.5 | | |
| Water | Add to the final weight | | | | | | |
| Appearance | Clear & one-phase liquid | Hazy, solid & liquid phases | Hazy | Opaque, oil & water phases | Clear & one-phase | Hazy | Opaque, oil & water phases |
| Form | LMBW | Liposome | Micelle solution | Emulsion | Alcohol solution | Micelle solution | Emulsion |
| Voriconazole Solubility (mg/mL) | 29.4 | 0.8 | 2.1 | 0.5 | 1.1 | 7.1 | 1.4 |

| Component | Concentration of each component (% wt over the total weight of each composition) | | | | | | | |
| --- | --- | --- | --- | --- | --- | --- | --- | --- |
| Lecithin | 25 | | | | 25 | 25 | | 25 |
| Glycocholic acid | | 10.6 | 10.6 | | 10.6 | | 10.6 | 10.6 |
| MCT | | | 15 | 15 | 15 | 15 | 15 | |
| Benzyl alcohol | 4.5 | | 4.5 | 4.5 | | 4.5 | 4.5 | 4.5 |
| Ethanol | 6.5 | | 6.5 | 6.5 | | 6.5 | 6.5 | 6.5 |
| Water | | | | Add to the final weight | | | | |
| Appearance | Hazy, solid & liquid phases | Opaque, oil & water phases | Hazy | Opaque, oil & water phases | Opaque, oil & water phases | Opaque, oil & water phases | Opaque, oil & water phases | Hazy |
| Form | Liposome | Emulsion | Micelle solution | Emulsion | Emulsion | Emulsion | Emulsion | Micelle solution |
| Voriconazole Solubility (mg/mL) | 13.7 | 3.1 | 7.6 | 19.4 | 0 | 19.8 | 8.0 | 8.0 |

The results indicate that (1) the LMBW composition dissolved voriconazole to a much higher concentration than any other combination of L, M, B and/or alcohol in water, and (2) except for the alcohol-only combination, only the LMBW composition was a clear and one-phase solution.

Example 3

The aim of this experiment was to use an LMBW vehicle to dissolve voriconazole to obtain a suitable IV injectable formulation that might be considered suitable to replace VFEND® I.V. for Injection. VFEND® I.V. for Injection is an antifungal drug approved by the FDA and marketed by Pfizer, Inc. in the US. VFEND® I.V. is supplied in a single-use vial containing a sterile lyophilized powder equivalent to 200 mg voriconazole and 3200 mg sulfobutyl ether beta-cyclodextrin sodium (SBECD). At high doses, cyclodextrin is known to cause kidney toxicity. The following voriconazole formulation in an LMBW vehicle (F96) could be developed as a safer substitute for VFEND® I.V. because F96 does not contain cyclodextrin.

| Composition (code F96) | Concentration (% w/w over the total weight of the F96 composition) |
| --- | --- |
| Voriconazole | 2 |
| Lecithin | 20.3 |
| Bile salt (glycocholic acid) | 10.6 |
| MCT | 6.5 |
| Ethanol | 6.1 |
| Benzyl alcohol | 4.5 |
| Propylene glycol | 5 |
| Edetate calcium disodium | 0.06 |
| NaOH and/or HCl | To adjust to pH 4* |
| Sterile water for injection (SWFI) | Add to final volume (about 44.9%) |

*In a separate study, voriconazole was found to be most stable in an aqueous solution at around pH 4. At pH 4, the F96 shelf life (expressed as T90, or the time when 10% voriconazole is degraded) is predicted to be >10 years at 5° C. and 1.6 years at 25° C.

F96 comprises 54.3% L, 17.4% M, and 28.3% B based on the Dry Weight, an Alcohol to Dry Weight ratio of 0.42/1, and a Water to Dry Weight ratio of about 1.2/1. F96 is within the LMBW zones as in FIGS. 1 and 2.

F96 was prepared as follows:
1. Weigh out and combine lecithin, MCT, bile acid (as a pH-adjusted stock solution in water), ethanol, benzyl alcohol, and propylene glycol in one glass container.
2. Gently mix until a clear one-phase solution, or an LMBW vehicle (F96 vehicle) is obtained. Note: there is no need for a high-energy mixer or homogenizer for this step.
3. Adjust pH to about 4 using HCl/NaOH.
4. Add voriconazole into the LMBW vehicle.
5. Mix until voriconazole is dissolved.
6. Add Sterile Water for Injection to the final weight.
7. Gently mix to obtain a clear and one-phase solution, i.e., a drug-containing LMBW.
8. Pass the solution through a sterile 0.2-micron filter.
9. Fill the filtrate into type-1 glass vials and seal the vials with rubber stoppers.

The vialed F96 formulation was a slightly yellow, clear and one-phase solution. F96 can be diluted freely with water, Normal Saline, D5W or another IV infusion fluid. The diluted solution remained clear and one-phase.

Example 4

The aim of this study was to demonstrate the utility of the F96 LMBW vehicle of Example 3 in dissolving a wide range of insoluble drugs. Twenty-two (22) insoluble drugs having a wide variety of chemical structures (including chemical element, small molecule, peptide and protein), properties and biological activities (including drugs, diagnostic agents and nutritional supplement agents) were selected and tested for solubility in F96 LMBW vehicle as follows:
1. Measure out a fixed amount of F96 vehicle.
2. Add a known amount of an insoluble drug substance.
3. Mix to dissolve the drug substance.
4. If the drug substance has completely dissolved, repeat Steps 1-3 until the F96 LMBW vehicle can no longer dissolve the added drug substance.
5. Record the maximum amount of the insoluble drug substance that the F96 LMBW vehicle could dissolve and use this value to calculate the drug's solubility in the F96 LMBW vehicle.

| Drug Name | Structure | Function | Solubility according to USP definition | Reported solubility in water (mg/mL) | Measured solubility in F96 LMBW Vehicle (mg/mL) |
| --- | --- | --- | --- | --- | --- |
| Amiodarone | Small molecule | Antiarrhythmic | Sparingly soluble | <0.5 | 118 |
| Amphotericin | Small molecule | Antifungal | Insoluble | <0.0001 | 2.4 |

-continued

| Drug Name | Structure | Function | Solubility according to USP definition | Reported solubility in water (mg/mL) | Measured solubility in F96 LMBW Vehicle (mg/mL) |
|---|---|---|---|---|---|
| Aprepitant | Small molecule | Antiemetic | Practically insoluble | <0.0001 | 12.7 |
| Camptothecin | Small molecule | Anticancer | Insoluble | <0.0001 | 0.5-1 |
| Casein | Protein | Nutritional supplement | Very poorly soluble | 0.001-0.0001 | 1 |
| Clarithromycin | Small molecule | Antibiotic | Practically insoluble | <0.0001 | 9.1 |
| Cyclosporine | Peptide | Immune suppressant | Very poorly soluble | 0.001-0.0001 | 8.1 |
| Celecoxib | Small molecule | Anti-inflammatory | Very poorly soluble | 0.001-0.0001 | 7.3 |
| Diazepam | Small molecule | Anti-anxiety | Very poorly soluble | 0.001-0.0001 | 17 |
| Ibuprofen | Small molecule | Anti-inflammatory | Sparingly soluble | 0.021 | 53.1 |
| Intraconazole | Small molecule | Antifungal | Insoluble | <0.0001 | 0.5-1 |
| Iodine | Element | Antiseptic and diagnostic agent | Sparingly soluble | 0.29 | 4 |
| Irinotecan HCl | Small molecule | Anticancer | Insoluble | <0.0001 | 20.4 |
| Levodopa | Small molecule | Anti-Parkinson's | Slightly soluble | 5 | 10 |
| Paclitaxel | Small molecule | Anticancer | Insoluble | <0.0001 | 1 |
| Phytonadione | Small molecule | Vitamin K | Insoluble | <0.0001 | 28.2 |
| Posaconazole | Small molecule | Antifungal | Insoluble | <0.0001 | 0.5 |
| Prednisolone Acetate | Small molecule | Steroid | Insoluble | <0.0001 | 1 |
| Progesterone | Small molecule | Steroid | Sparingly soluble | 0.017 | 12.0 |
| Propofol | Small molecule | Anesthetic | Insoluble | <0.0001 | 50.8 |
| Resveratrol | Small molecule | Antiaging or cosmetic agent | Insoluble | <0.0001 | 9 |
| Tyrosine | Small molecule | Amino acid | Sparingly soluble | 0.45 | 1 |
| Voriconazole | Small molecule | Antifungal | Insoluble | 0.7 | 20 |

All above drugs are known to have exceptionally low solubility in water. Regardless of their chemical structure or biological activity, the solubility for every drug tested was substantially increased in the F96 LMBW vehicle. The drug concentration achieved by F96 LMBW in the above table ranged from 0.5 mg/mL to 118 mg/mL (equivalent to 0.05% to 11.8% w/v based on the total composition volume, or approximately 0.05% to 11.8% w/w based on the total composition weight, or 0.0015/1-0.36/1 in terms of drug weight ratio to the Dry Weight). These findings demonstrate that LMBWs are Universal Solubilizers.

Example 5

A pharmacokinetic study of the F96 voriconazole formulation as prepared in Example 3 was performed in beagle dogs. Eight dogs (4 male and 4 female) were used in this study. A single dose of 3.0 mg voriconazole/kg in F96 was administered intravenously (IV) to each dog in the test, and blood samples were collected at 0.083, 0.25, 0.50, 1.0, 1.5, 2, 4, 6, 8, 12, and 24 hours following IV administration. For comparison, the pharmacokinetic study of the reference listed drug VFEND®, I.V. for Injection was performed using the same procedure and dogs. The voriconazole concentration in plasma was analyzed by HPLC-Mass Spectroscopy. The results obtained are shown in the table F96 exhibits a very similar pharmacokinetic profile to VFEND®, I.V. for Injection. No adverse reactions were observed in the dogs receiving F96. These findings indicate that F96 is safe for intravenous injection and can provide the same pharmacokinetic profile as (i.e., is bioequivalent to) the cyclodextrin-containing VFEND®, I.V for Injection.

| Group | Animal# & Sex | $T_{1/2}$ (hr) | $AUC_{last}$ (hr * ng/mL) | $AUC_{INF\ obs}$ (hr * ng/mL) | $AUC_{\%Extrap\ obs}$ (%) | $V_{ss\_obs}$ (mL/Kg) | $Cl_{obs}$ (mL/hr/Kg) | $MRT_{last}$ (hr) |
|---|---|---|---|---|---|---|---|---|
| LMBW | 8471330M | 15.2 | 32074 | 47992 | 33.2 | 1348 | 62.5 | 9.46 |
| | 8544906M | 8.15 | 33834 | 39126 | 13.5 | 929 | 76.7 | 8.41 |
| | 8556742F | 5.23 | 31371 | 32911 | 4.68 | 768 | 91.2 | 7.29 |

-continued

| Group | Animal# & Sex | $T_{1/2}$ (hr) | $AUC_{last}$ (hr * ng/mL) | $AUC_{INF\ obs}$ (hr * ng/mL) | $AUC_{\%Extrap\ obs}$ (%) | $V_{ss\_obs}$ (mL/Kg) | $Cl_{obs}$ (mL/hr/Kg) | $MRT_{last}$ (hr) |
|---|---|---|---|---|---|---|---|---|
| | 8555274F | 9.39 | 30218 | 36341 | 16.8 | 1097 | 82.6 | 8.38 |
| | 8677655M | 10.8 | 30360 | 38115 | 20.3 | 1171 | 78.7 | 8.56 |
| | 8675997M | 3.94 | 29803 | 30393 | 1.94 | 719 | 98.7 | 6.84 |
| | 8565602F | 7.89 | 29927 | 33696 | 11.2 | 937 | 89.0 | 7.40 |
| | 8542113F | 2.75 | 16836 | 16895 | 0.350 | 911 | 178 | 5.05 |
| | Total | 8 | 8 | 8 | 8 | 8 | 8 | 8 |
| | Average | 7.93 | 29302.91 | 34433.77 | 12.76 | 985.04 | 94.61 | 7.67 |
| | Std Dev | 4.04 | 5216.80 | 8862.72 | 10.89 | 209.84 | 35.24 | 1.35 |
| VFEND | 8471330M | 10.2 | 32039 | 39657 | 19.2 | 1074 | 75.6 | 8.39 |
| | 8544906M | 8.14 | 41040 | 47285 | 13.2 | 756 | 63.4 | 8.29 |
| | 8556742F | 3.94 | 28154 | 28685 | 1.85 | 724 | 105 | 6.50 |
| | 8555274F | 6.56 | 30924 | 33631 | 8.05 | 852 | 89.2 | 7.46 |
| | 8677655M | 19.0 | 39232 | 66316 | 40.8 | 1212 | 45.2 | 9.79 |
| | 8675997M | 4.93 | 16497 | 19841 | 16.9 | 1028 | 151 | 4.30 |
| | 8565602F | 16.0 | 37483 | 56212 | 33.3 | 1156 | 53.4 | 8.93 |
| | 8542113F | 2.44 | 20585 | 20627 | 0.205 | 808 | 145 | 5.51 |
| | Total | 8 | 8 | 8 | 8 | 8 | 8 | 8 |
| | Average | 8.9 | 30744.4 | 39031.8 | 16.7 | 951.3 | 91.0 | 7.4 |
| | Std Dev | 5.89 | 8767.43 | 16696.19 | 14.37 | 189.32 | 40.14 | 1.84 |

Figure 6:
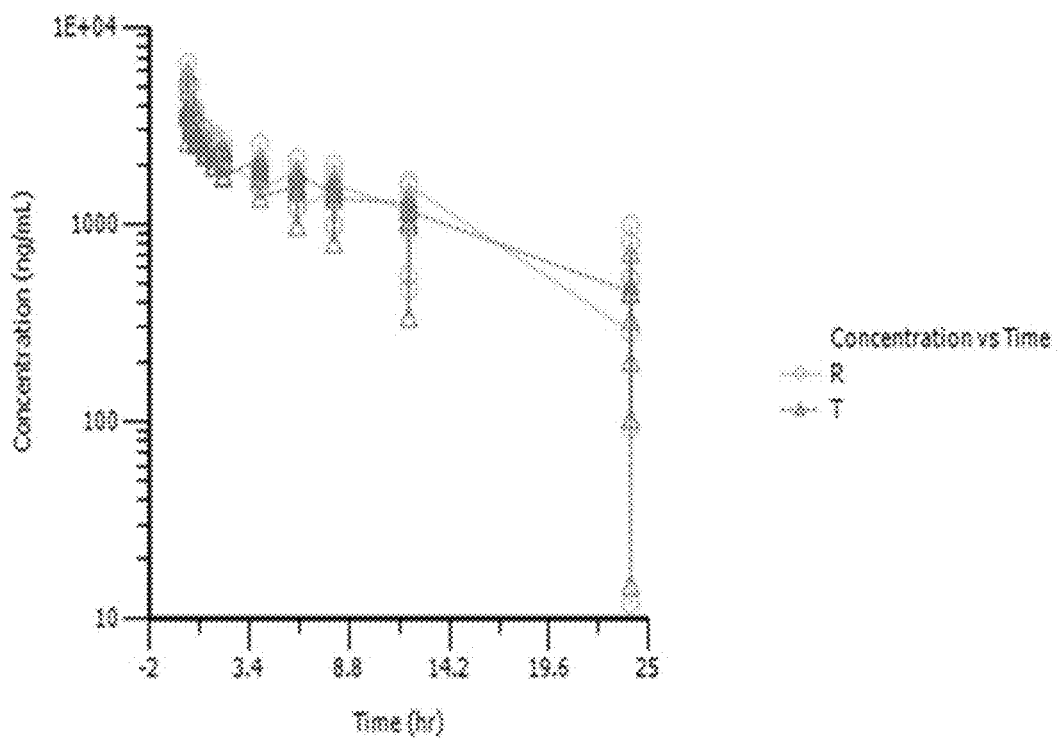
FIG. 6 illustrates plasma concentration over time profiles of voriconazole in VFEND® (denoted as R) and an LMBW formulation (F96, Example 5, denoted as T) following intravenous injection into beagle dogs at 3 mg/kg dose.

F96 exhibits a very similar pharmacokinetic profile to VFEND®, I.V. for Injection (FIG. 6). No adverse reactions were observed in the dogs receiving F96. These findings indicate that F96 is safe for intravenous injection and can provide the same pharmacokinetic profile as (i.e., is bioequivalent to) the cyclodextrin-containing VFEND®, I.V for Injection.

Example 6

The aim of this experiment was to evaluate the safety of the F96 LMBW (without a drug) in beagle dogs (2 males and 2 females) following intravenous injection. F96 was diluted in Normal Saline and administered IV daily for 4 weeks at 0 (the F96 LMBW vehicle only), 8 mg/kg and 12 mg/kg (corresponding to about 4-6 mL of F96 LMBW per day). Clinical and post mortem observations included body weight, body temperature, ophthalmological examination, ECG, blood cell count, blood biochemistry, urinalysis, bone marrow smears, gross anatomy, organ weights (12 organs) and histological studies (liver, kidney, lung).

F96 was well-tolerated in the test animals without hemolysis or acute adverse events observed during the 4-week study. There were no noticeable post mortem pathological observations at the completion of the study. These findings indicate that the LMBW composition is safe for injection.

Example 7

The aim of this experiment was to determine whether an LMBW could be successfully made using lecithin from a natural source (soy or egg) or a synthetic (DMPC) phospholipid. The following compositions were prepared using methods like those in Example 1, and then were visually and microscopically examined.

| Ingredient name | Composition Code Concentration (% w/w over the total weight of the composition) | | | | |
|---|---|---|---|---|---|
| | F100 | F102 | F104 | F106 | F116 |
| Soy lecithin (Phospholipon 90G) | 20.3 | | | | |
| Soy lecithin (LIPOID S100) | | 20.3 | | | |
| Egg lecithin (LIPOID E80) | | | 20.3 | | |
| Synthetic phosphatidylcholine (DMPC) | | | | 20.3 | |
| Soy lecithin (LIPOID S75) | | | | | 20.3 |
| Bile acid (glycocholic acid) | 10.6 | | | | |
| MCT | 6.5 | | | | |
| Ethanol | 6.1 | | | | |
| Benzyl alcohol | 4.5 | | | | |
| Edetate calcium disodium | 0.06 | | | | |
| NaOH/HCl | pH adjustment to 4.5 | | | | |
| Sterile water for injection (SWFI) | Add to the final weight (about 51.9%) | | | | |

Each of the above compositions (F100, F102, F104, F106 and F116) comprises 54.3% lecithin (soy lecithin, egg lecithin or DMPC), 17.4% MCT and 28.3% bile salt based on the Dry Weight, an Alcohol to Dry Weight ratio of 0.28/1 and a Water to Dry Weight ratio of about 1.39/1. Each of the compositions above is within the LMBW zone as defined in FIG. 1.

All compositions made with the different soy lecithin (Phospholipon 90G, LIPOID S100 and LIPOID S75) were clear and one-phase solutions. The phosphatidylcholine (PC) contents in Phospholipon 90G, LIPOID S100 and LIPOID S75 are about 90%, 100%, and 75%, respectively. The egg lecithin composition was hazy and the DMPC composition phase separated. These findings indicate that soy lecithin is the preferred ingredient for an LMBW.

Example 8

The aim of this study was to determine whether long chain triglycerides (LCT), as found in vegetable oils, could substitute for MCT in an LMBW. The following compositions were prepared and tested using the same protocol as Example 7.

| Ingredient name | Composition Code Concentration (% w/w over total weight of the final composition) | |
| --- | --- | --- |
| | F100 | F101 |
| Soy lecithin | 20.3 | 20.3 |
| Bile acid (glycocholic acid) | 10.6 | 10.6 |
| Sesame oil (LCT) | | 6.5 |
| MCT | 6.5 | |
| Ethanol | 6.1 | |
| Benzyl alcohol | 4.5 | |
| Edetate calcium disodium | 0.06 | |
| NaOH/HCl | pH adjustment to 4.5 | |
| Sterile water for injection (SWFI) | Add to the final weight (about 51.9%) | |

Each of the above compositions (F100 and, F101) comprises 54.3% wt lecithin, 17.4% wt MCT or LCT and 28.3% wt bile acid based on the Dry Weight, an Alcohol to Dry Weight ratio of 0.28/1 and a Water to Dry Weight ratio of about 1.39/1. Each of the compositions above is within the LMBW zones as defined in FIG. 2 and FIG. 3.

The F100 composition made with MCT was a clear and one-phase solution. F101 made with same amount of LCT separated into different phases. These findings indicate that MCT is the preferred ingredient for an LMBW.

Example 9

The aim of this experiment was to determine whether an LMBW could be made using lecithin from different sources and either of two commonly used pharmaceutical bile salts, namely, sodium glycocholate and sodium deoxycholate. Each of the two different bile salts was tested in two different LMBW compositions. The following compositions were prepared and tested using the same protocol as Example 7.

| Ingredient name | Composition Code Concentration (% w/w over the total weight of the composition) | | | |
| --- | --- | --- | --- | --- |
| | F100 | F110 | F116 | F117 |
| Soy lecithin (Phospholipon 90G) | 20.3 | | | |
| Soy lecithin (LIPOID S100) | | 20.3 | | |
| Soy lecithin (LIPOID S75) | | | 20.3 | 20.3 |
| Bile salt (glycocholic acid) | 10.6 | | 10.6 | |
| Bile salt (deoxycholic acid) | | 10.6 | | 10.6 |
| MCT | 6.5 | | | |
| Alcohol | 6.1 | | | |
| Benzyl alcohol | 4.5 | | | |
| Edetate calcium disodium | 0.06 | | | |
| NaOH/HCl | pH adjustment to 4.5 | | | |
| Sterile water for injection (SWFI) | Add to the final weight (about 51.9%) | | | |

Each of the above compositions (F100, F110, F116 and F117) contains 54.3% lecithin, 17.4% MCT and 28.3% bile salt based on the Dry Weight and an Alcohol to Dry Weight ratio of 0.28/1 and Water to Dry Weight ratio of about 1.39/1. Each of the compositions above is within the LMBW zone as defined in FIG. 1.

All of the tested compositions (F100, F110, F116 and F117) produced clear and one-phase solutions. These findings indicate that lecithin from different sources and a bile salt made from either glycocholic acid or deoxycholic acid can be used to make an LMBW.

Example 10

The aim of this experiment was to determine whether an LMBW can be made in the F100 composition (as in Example 7) at pH 3.9, 4.1, 4.4, 4.8, 6.9 or 8.7. Each composition was prepared and tested using the same protocol as Example 7.

All F100 compositions prepared at pH between 3.9 and 8.7 were clear and one-phase solutions. These findings indicate that the acceptable pH range for an LMBW is about from pH 3.5 to pH 9.

Example 11

The aim of this experiment was to determine whether an LMBW composition (F100 as in Example 7) could be diluted with water or an IV infusion fluid and remain as a clear, one-phase solution. F100 was prepared according to the same procedure as in Example 7, and then mixed with Sterile Water for Injection USP (SWFI) or the IV infusion fluids 5% Dextrose Injection USP ("D5W") and 0.9% Sodium Chloride Injection USP ("Normal Saline or NS"), at volume ratios of 1:10 and 1:100. Each mixture was gently mixed (10 inversions by hand). After 0, 2, 4, and 24 hours at room temperature, the appearance of each mixture was examined visually and microscopically for clarity, precipitation, and phase separation. In addition, osmotic pressure was measured for each diluted solution after 24 hours.

All diluted mixtures were colorless, clear and one-phase liquids. The measured osmotic pressure values (mOsm/kg) are shown in the table below:

| Dilution Ratio (volume of F100:volume of diluent) | Osmotic Pressure (mOsM) | | |
| --- | --- | --- | --- |
| | SWFI | D5W | NS |
| 1:10 | 157 | 423 | 429 |
| 1:100 | 17 | 286 | 304 |

These findings indicate that an LMBW can be diluted freely with water or an IV infusion fluid. The D5W- and NS-diluted LMBW mixtures are near-isotonic and are thus suitable for IV infusion.

Example 12

The aim of this experiment was to determine the stability of an LMBW composition (F100). F100 was prepared according to the same procedure as in Example 7. The composition's pH was adjusted to 7.2 with NaOH, filtered through a 0.2-micron filter, filled into type-1 glass vial (5 mL/vial) and sealed with rubber stoppers (Flurotec® stoppers). The vials were placed in both upright and inverted positions in 2-8° C., 25° C., 30° C. and 40° C. stability chambers. Sample evaluations were performed at time zero, 1, 2, 3, 6 and 12 months, at which visual examinations and pH determinations were performed.

After 12 months, the F100 LMBW remained as a clear and one-phase solution in all vials, without any sign of particles, precipitation or cloudy appearance. The pH remained between 6.0 and 7.0 in all vials tested.

These findings indicate that an LMBW composition is stable in terms of maintaining its clear and one-phase properties and pH for an extended period.

Example 13

The aim of this experiment was to determine the presence of any particles in an LMBW composition. An LMBW composition (F100) was prepared according to the same procedure as in Example 7 and was evaluated using the following test methods:

Method #1: Visual examination, which can detect particles down to about 50 microns.
Method #2: Light microscopy (Nikon, ECLIPSE 50i), which can detect particles down to about 0.1 micron.
Method #3: Dynamic laser light scattering spectrometry (Malvern Zetasizer, Model Nano-ZS), which has a particle sizing range between 0.3 nm to 10 microns.

F100 was evaluated by all three methods in both undiluted and diluted form (with water at dilution ratio of 1:10 and 1:100 in volume of F100: volume of diluent). In all samples tested, none of the methods detected the presence of any particles. These findings indicate that an LMBW is substantially free of any nanometer to micron-sized particles, droplets or structures. This observation clearly demonstrates that an LMBW composition is NOT a liposome, emulsion, suspension, micellar dispersion or other multiple phase system that could be readily detected by the methods employed above.

Example 14

The aim of this experiment was to determine the minimal water content for an LMBW. The following LMBW compositions were prepared using the same procedure as in Example 7. The concentration of L, M and B are all in the LMBW zone as shown in FIG. 1. Each composition was adjusted to pH 7.2 and was found to be clear and one-phase, i.e., being an LMBW.

| Composition Code | Concentration (% w/w based on the total weight of the final composition) | | | | | | | | | | | | | | |
|---|---|---|---|---|---|---|---|---|---|---|---|---|---|---|---|
| | H | O | IQ | NO | NH | PI | OP | I | AE | GH | EJ | BE | BEK | G | N |
| Lecithin | 24 | 22 | 18 | 23 | 24 | 20 | 19 | 20 | 26 | 25 | 18 | 12 | 12 | 26 | 24 |
| MCT | 4 | 8 | 6 | 8 | 6 | 6 | 8 | 4 | 0 | 4 | 2 | 0 | 2 | 4 | 4 |
| Bile salt (glycocholate) | 12 | 10 | 16 | 9 | 10 | 14 | 13 | 16 | 14 | 11 | 20 | 28 | 26 | 10 | 12 |
| Ethanol | 5 | 5 | 5 | 5 | 5 | 5 | 5 | 5 | 5 | 5 | 5 | 5 | 5 | 5 | 5 |
| Benzyl alcohol | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| Water | Add to the final weight | | | | | | | | | | | | | | |

To test the minimal amount of water needed to maintain the clear and one-phase appearance, each composition was vacuum-dried to remove water and ethanol to obtain the anhydrous LMBW. Some of the anhydrous LMBWs were not clear and underwent phase separation. To each anhydrous LMBW, ethanol was added back to the original concentration (5% wt over the final weight) and then water was added back with mixing in small portions until a clear and one-phase solution was obtained. The amount of water added was recorded and its concentration in the re-hydrated LMBW was calculated (listed in the table below) and was regarded as the minimal water needed to form an LMBW.

These findings indicate that an LMBW composition requires a minimal amount of water of 0.1/1 in Water to Dry Weight Ratio.

Example 15

An LMBW formulation containing the insoluble drug diazepam was tested in animals and human for safety and pharmacokinetic profiles following a subcutaneous injection. Solubility of the benzodiazepine in water is about 0.05 mg/mL. The LMBW formulation is provided as a ready-to-use aqueous solution having the following composition.

| Name | % (w/w based on total weight of the final composition) |
|---|---|
| Diazepam | 1.7 (about 17 mg/mL) |
| Lecithin | 20.3 |
| MCT | 6.5 |
| Bile salt (glycocholic acid) | 10.6 |
| Benzyl alcohol | 4.5 |
| Ethanol | 6.1 |
| Calcium disodium ededate | 0.06 |
| Methionine | 0.15 |
| Sterile Water for Injection | add to the final weight |
| HCl/NaOH | to adjust pH |

The concentrations of L, M and B in the above formulation are respectively 54.3%, 17.4% and 28.3% based on the Dry Weight and are within the LMBW zone as shown in FIG. 1.

The above formulation was prepared by the following steps:
1. Weigh out and add bile salt to the 1$^{st}$ container.
2. To the 1$^{st}$ container, weigh out and add Sterile Water for Injection and mix to form a uniform suspension.
3. To the 1$^{st}$ container, weigh out and add a NaOH solution and mix until the clear solution is obtained.
4. To the 1$^{st}$ container, weigh out and add calcium disodium edetate and methionine and mix to dissolve.
5. Weigh out and add diazepam drug substance into a 2nd container.
6. To the 2nd container, weigh out and add ethanol, benzyl alcohol and MCT and mix to dissolve.
7. To the 2nd container, weigh out and add lecithin and mix to dissolve.
8. Combine the contents in the first container with the contents in the 2nd container.

| Composition Code | Minimal water concentration needed for an LMBW (in Water to Dry Weight Ratio) | | | | | | | | | | | | | | |
|---|---|---|---|---|---|---|---|---|---|---|---|---|---|---|---|
| | H | O | IQ | NO | NH | PI | OP | I | AE | GH | EJ | BE | BE | G | N |
| Water to Dry Weight Ratio | 0.8/1 | 0.8/1 | 0.1/1 | 0.3/1 | 0.3/1 | 0.1/1 | 0.1/1 | 0.2/1 | 0.3/1 | 0.3/1 | 0.2/1 | 0.3/1 | 0.3/1 | 0.6/1 | 0.5/1 |

9. Adjust pH to about 8 using HCl/NaOH.
10. Mix until a clear and one-phase solution is obtained. Add Sterile Water for Injection to the final weight.
11. Pass the solution through a 0.2 μm sterilizing filter. Fill the filtrate into sterile glass vials and seal the vials with rubber stoppers.
12. Optionally, autoclave the sealed vials. Cap and keep at room temperature.

The formulation was first tested in rodents (2.25 mL/kg) and rabbits (0.57 mL/injection site) and was found to be safe both systemically and at the injection site. Subsequently, the formulation was tested in human subjects (10 mg dose) for safety and pharmacokinetic in a US Phase-1 clinical trial under an IND approved by FDA. The formulation was found to be generally safe and well-tolerated in human subjects, and generated the following pharmacokinetic parameters with a subcutaneous injection of a 10 mg diazepam dose:

| Parameter (Units) | Mean (C.V. %) (n = 16 human subjects) |
|---|---|
| $C_{max}$ (ng/mL) | 122.65 (35.2) |
| $T_{max}$ (hours) | 4.00 (2.00-8.00) |
| $AUC_{0-T}$ (ng × h/mL) | 6194.45 (33.7) |
| $AUC_{0-Inf}$ (ng × h/mL) | 6688.23 (34.8) |
| $\lambda_z$ (hours$^{-1}$) | 0.0144 (37.7) |
| $T_{half}$ (hours) | 55.46 (40.9) |

Example 16

The following four LMBW formulations were tested for viscosity, particle size and light transmittance:

| | Concentration (% w/w over the total weight of the formulation) | | | |
|---|---|---|---|---|
| Formulation code | F95V | F95 | F96V | F96 |
| Voriconazole | 0 | 0 | 0 | 2 |
| Diazepam | 0 | 1.7 | 0 | 0 |
| Lecithin | 20.3 | 20.3 | 20.3 | 20.3 |
| Bile salt (glycocholic acid) | 10.6 | 10.6 | 10.6 | 10.6 |
| MCT | 6.5 | 6.5 | 6.5 | 6.5 |
| Alcohols | 10.6 | 10.6 | 15.6 | 15.6 |
| EDTA | 0.06 | 0.06 | 0.06 | 0.06 |
| Sterile water for injection | Add to final volume | | | |

Each above formulation contains 54.3% lecithin, 17.4% MCT and 28.3% bile salt based on the Dry Weight and is within the LMBW zone as defined in FIG. 1.

Instruments used are as follow:

| Test | Instrument | Maker | Model |
|---|---|---|---|
| Viscosity | Rheometer | Brookfield | RVDV-III |
| Particle sizer | Dynamic light scattering spectrometer | Malvern | Zetasizer Nano-ZS |
| Light transmittance | UV-vis Spectrophotometer | Beckman | Du640 |

Viscosity test method and results:
1. Set up the rheometer at temperature 25° C.
2. Install a cone-plate 40 well on the rheometer.
3. Load 0.5 mL viscosity standard to calibrate the instrument, then clean and dry the well.
4. Load 0.5 mL sample into the well, set the speed at 10 rpm, start testing.

| Sample | F95V | F95 | F96V | F96 |
|---|---|---|---|---|
| Viscosity (cP) | 111 | 115 | 67.4 | 70.6 |

Light transmittance test method and result:
1. Blank the instrument with an empty 10-mm light pass length quartz cuvette (air as blank)
2. Fill the cuvette with a formulation (undiluted or diluted with 5% dextrose solution at 20×)
3. Measure light transmittance at 700, 800, 900 and 1000 nm wavelength

| | Light Transmittance (without dilution) | | | | |
|---|---|---|---|---|---|
| Sample | Wavelength (nm) | F95V | F95 | F96V | F96 |
| Light Transmittance (%) | 700 | 106.1 | 105.3 | 104.1 | 107.1 |
| | 800 | 104.9 | 103.3 | 103.3 | 105.9 |
| | 900 | 100.3 | 98.2 | 98.9 | 100.9 |
| | 1000 | 83.6 | 82.9 | 83.5 | 85.4 |

| | Light Transmittance (20x dilution with D5W) | | | | |
|---|---|---|---|---|---|
| Sample | Wavelength (nm) | F95V | F95 | F96V | F96 |
| Light Transmittance (%) | 700 | 99.6 | 99.8 | 99.7 | 99.5 |
| | 800 | 99.9 | 99.9 | 100.1 | 99.0 |
| | 900 | 99.8 | 99.9 | 100.0 | 99.7 |
| | 1000 | 101.0 | 101.0 | 101.2 | 101.1 |

Particle sizing test method and results:
1. Load 1 mL sample (undiluted or 20× or 100× diluted in D5W) into a cuvette
2. Enter the viscosity value measured in the above viscosity study
3. Start the measurement

| Sample | F95V (undiluted or D5W diluted 20X & 100X) | F95 (undiluted or D5W diluted 20X & 100X) | F96V (undiluted or D5W diluted 20X & 100X) | F96 (undiluted or D5W diluted 20X & 100X) |
|---|---|---|---|---|
| Average size (Z-avg, nm) | <0.6 | <0.6 | <0.6 | <0.6 |
| Measurement quality | Poor* | Poor* | Poor* | Poor* |

*Because size is below the instrument limit (0.6 nm)

Example 17

Bile salt is known to be hemolytic. In this study, the following three bile salt containing compositions were tested and compared for their hemolytical potential in lysing rabbit red blood cells (RRBC). Their hemolytical potential was also compared to sulfobutylether-β-cyclodextrin (SBECD) aqueous solution. SBECD is the solubilizer used for currently marketed voriconazole drug (VFEND®, containing 19.2% SBECD in water) and other drugs. The LMBW formulation tested herein contains 54.3% lecithin, 17.4% MCT and 28.3% bile salt based on the Dry Weight and is within the LMBW zone as defined in FIG. 1.

| Component | Compositions (% w/w) | | | |
|---|---|---|---|---|
| | LMBW (L + M + B + W) | Mixed Micelle (L + B + W) | Bile salt only (B + W) | SBECD solution |
| Lecithin | 8.12 | 5.86 | 0 | 0 |
| Bile salt (glycocholic acid) | 4.24 | 4.24 | 4.24 | 0 |
| MCT | 2.6 | 0 | 0 | 0 |
| SBECD | 0 | 0 | 0 | 19.2 |
| Water | 85.04 | 89.91 | 95.76 | 80.8 |

Each composition was mixed with the same amount of RRBC and diluted to 25 times or to a final bile salt concentration of 0.17% w/v with normal saline. Normal saline and DI-water used as negative and position control respectively. The mixture was incubated at 37° C. for 15 minutes to allow for hemolysis to take place. After incubation, each sample was centrifuged at 5000 rpm to separate the intact RRBC (in the pellet) from the hemolyzed components (in the supernatant). A UV absorbance measured was performed for the supernatant (containing the hemolysis product or heme) using a spectrophotometer at 416 nm to determine the concentration of heme. The absorbance value from positive control or DI-water sample was considered as 100% hemolysis and used to calculate the degree of hemolysis of other samples.

| Sample | Degree of hemolysis (%) |
|---|---|
| DI-water (positive control) | 100 |
| Normal saline | 4.8 |
| LMBW | 3.0 |
| LBW | 15.0 |
| Bile salt solution | 10.0 |
| SBECD solution | 4.7 |

The results indicated that LMBW formulation is less hemolytic than the bile salt only solution or the mixed micelle composition and is comparable to normal saline or the SBECD solution. The findings suggest that the LMBW formulation can significantly reduce the hemolytic activity of bile salt, rendering the LMBW a safer formulation to use than the bile salt-containing formulations such as a bile salt only solution or a mixed micelle solution.

Example 18

This study was performed to explore the limits of water and alcohol contents in LMBW composition (such as F95V in Example 16). To prepare a LMBW with different water or alcohol content, the following procedure was used:

Step 1. Preparation of aqueous phase: add glycocholic acid and other water soluble components in water, increase pH to 10-11 using 10N NaOH and mix to obtain a clear solution.

Step 2. Preparation of oil phase: add lecithin, MCT and other oil-soluble components in ethanol and mix to form a clear solution.

Step 3: Add aqueous phase (step 1) into oil phase (step 2) and mix to obtain a uniform solution.

Step 4: Adjust pH to 4-8.

Step 5: Remove ethanol completely by vacuum drying and water partially to a predetermined content level.

Step 6: Add ethanol as needed to a pre-determined content.

It was discovered that water content in this LMBW composition can be adjusted upward from about 0.1/1 (the lower limit in Water to Dry Weight Ratio) to no upper limit and alcohol content can be adjusted from 0/1 to about 1.6/1 (the upper limit in Alcohol to Dry Weight Ratio). When water is at or below the 0.1/1 lower limit or alcohol is at or above the 1.6/1 upper limit, precipitation occurred (see table below).

| % (w/w based on total weight of the final composition) | F145V | F146V | F129V | F132V |
|---|---|---|---|---|
| Lecithin | 20.3 | 20.3 | 20.3 | 20.3 |
| Bile salt (in Glycocholic acid) | 10.6 | 10.6 | 10.6 | 10.6 |
| MCT | 6.5 | 6.5 | 6.5 | 6.5 |
| Ethyl alcohol | 44.9 | 0 | 48.9 | 60.6 |
| Benzyl alcohol | 4.5 | 0 | 4.5 | 0 |
| Calcium disodium Edetate | 0.06 | 0 | 0.06 | 0 |
| Methionine | 0.15 | 0 | 0.15 | 0 |
| 4N NaOH | 5 | 3.4 | 5 | 2 |
| Sterile water for injection (SWFI) | 8 | 59.1 | 4 | 0 |
| Water to Dry Weight Ratio | 0.2/1 | 1.6/1 | 0.1/1 | 0/1 |
| Alcohol to Dry Weight Ratio | 1.2/1 | 0/1 | 1.3/1 | 1.6/1 |
| Appearance | A clear one-phase solution | A clear one-phase solution | Precipitated (exceeded the lower water limit) | Precipitated (exceeded the upper alcohol limit) |

A reduced water content such as 0.2/1 in F145V can improve chemical stability of certain drug substances which are sensitive to water such as voriconazole. The addition of alcohol can further increase solubility of an insoluble drug in a LMBW. On the other hand, the reduction or removal of alcohol can improve the safety of a LMBW.

Example 19

A LMBW (F145V as in Example 18, containing 8% w/w water or 0.2/1 Water to Dry Weight Ratio) was used to solubilize the insoluble drug voriconazole to about 20 mg/mL. The pH of the solubilized solution was adjusted with NaOH and HCl and the resulted solutions were stored at 2-8° C. It was discovered the solution precipitated when the pH is lower than 4, turned hazy, i.e. no longer one-phase when pH is above 8, but remained clear and one-phase at a pH between 4 and 8. Therefore, for the F145V LMBW composition, the preferred pH range is from about pH 4 to about pH 8.

Example 20

Voriconazole solubility in water is very low at about 0.7 mg/mL at 25° C. This study was to determine solubility of voriconazole in the F145V LMBW composition (as prepared in Example 18) in its undiluted form and after being diluted with an IV infusion fluid. Different amounts of voriconazole (20 to 60 mg/mL) were first dissolved in F145V and subsequently diluted in an IV infusion fluid, such as normal saline (NS), 5% dextrose in water (D5W), water for injection (WFI), or Lactated Ringers solution, to a final voriconazole concentration of about 0.5 to 5 mg/mL. The undiluted and diluted solutions were visually inspected for precipitation at RT for 24 hours.

Solubility of Voriconazole in F145V:

| Voriconazole added to F145V (mg/mL) | Appearance of the undiluted solutions | Appearance of the solutions after being diluted in an IV infusion fluid |
| --- | --- | --- |
| 20 | Clear & one-phase solution | Clear & one-phase solution |
| 30 | Clear & one-phase solution | Clear & one-phase solution |
| 40 | Clear & one-phase solution | Slight precipitation |
| 50 | Clear & one-phase solution | Major precipitation |
| 60 | Clear & one-phase solution | Major precipitation |

The findings indicated that F145V, in the undiluted form, can increase voriconazole solubility profoundly from about 0.7 mg/mL to ≥60 mg/mL (86 folds increase). This undiluted solution is clear and one-phase and is ready-to-use for direct injection. For an IV infusion in which an IV Infusion Fluid is used to dilute the drug to obtain a larger volume, the solution containing 30 mg/mL voriconazole in F145V can be used as a "concentrate" formulation, which can be freely diluted in an IV Infusion fluid at a final voriconazole concentration between 0.5 and 5 mg/mL without any precipitation.

Example 21

Both F95V (Example 16) and F145V (Example 18) LMBW contain 10.6% (w/w) bile salt (glycocholic acid) in the final composition. Their preparation procedure involves conversion of glycocholic acid to sodium glycocholate (i.e. bile salt) by adding sodium hydroxide. It was discovered that for LMBW the mixing ratio of sodium hydroxide to glycocholic acid must be between about 1:8 (w:w) and 1:10 (w:w) (sodium hydroxide:glycocholic acid). The 1:8 (w:w) and 1:10 (w:w) correspond to 1.5:1 and 1:1 in molar ratio, respectively. It was discovered that when the mixing ratio of sodium hydroxide:bile acid is below 1:10 (w:w), precipitation occurred, and when mixing ratio of of sodium hydroxide: bile acid is above 1:8 (w:w), the composition became cloudy.

Example 22

A LMBW vehicle (F101V) was tested to its ability to dissolve a lyophilized voriconazole powder in vials.

The Composition of F101V:

| Name | % (w/w based on total weight of the final composition) |
| --- | --- |
| Lecithin | 20.3 |
| Bile salt (Glycocholic acid) | 10.6 |
| MCT | 6.5 |
| Alcohol (Ethyl alcohol) | 5.0 |
| Propylene glycol | 15.0 |
| Benzyl alcohol | 1 |
| Calcium disodium Edetate | 0.06 |
| Sterile water for injection (SWFI) | 41.54 |

To prepare a lyophilized voriconazole in vials, voriconazole was first dissolved in a cosolvent containing tert-butanol and water to form a clear solution. The solution was passed through a 0.2-micron filter, filled into vials (200 mg voriconazole/vial), and lyophilized to obtain lyophilized voriconazole in powder or cake-like solid form ("Lyophile"). The Lyophile is insoluble in water.

To dissolve or reconstitute the lyophilized voriconazole in the vials, the F101V vehicle was added into the vials via a syringe and needle. The F101V was able to dissolve the lyophilized voriconazole completely to form a clear and one-phase solution within 1 minute of gentle shaking. The final voriconazole concentration was about 10-20 mg/mL without any visible particles. Therefore, a LMBW can be used as a vehicle to dissolve or reconstitute an insoluble drug in a lyophilized form to obtain a clear and one-phase solution which is ready to use.

Example 23

Stability of voriconazole in the LMBW F145V (Example 18) was tested. A batch of F145V was prepared according to the procedure in Example 18. Voriconazole was dissolved in F145V to form a clear and one-phase solution containing 30 mg/mL voriconazole. The solution was passed through a 0.2-micron filter to sterilize, fill in to glass vials (200 mg/vial). The sealed vials were stored at 4 different temperatures (2-8° C., 25° C., 30° C., and 40° C.). After 0, 1, and 2 months, sample vials were tested for appearance, pH, clarity, particulate matter, voriconazole assay/impurities, osmolarity and viscosity. The stability test results are summarized in the following table:

Formulation code: F145V
Formulation batch No. LPI245-4-19
Batch size: 200 g
Stability condition: 30 mg/mL voriconazole in F145V,
stored at 2-8, 25, 30, and 40° C.
Vial orientation: Upstand
Manufactured by Latitude Pharmaceuticals Inc.

| Test | Storage Temperature (° C.) | Day 0 | 1 month | 2 months |
|---|---|---|---|---|
| Appearance | 2 to 8 | C&OP* | No change | No change |
|  | 25 |  | No change | No change |
|  | 30 |  | No change | No change |
|  | 40 |  | No change | No change |
| pH | 2 to 8 | 6.03 | 6.02 | 5.91 |
|  | 25 |  | 6.05 | 6.06 |
|  | 30 |  | 6.05 | 6.09 |
|  | 40 |  | 6.06 | 6.12 |
| Assay (mg/mL) | 2 to 8 | 30.3 | 31.6 | 31.5 |
|  | 25 |  | 31.5 | 30.6 |
|  | 30 |  | 31.1 | 30.6 |
|  | 40 |  | 30.2 | 29.7 |
| Assay recovery (% over the Day 0 value) | 2 to 8 | 100 | 103 | 103 |
|  | 25 |  | 103 | 100 |
|  | 30 |  | 102 | 100 |
|  | 40 |  | 99 | 97 |
| Purity (% wt. over initial wt. of voriconazole) | 2 to 8 | 100 | 103 | 103 |
|  | 25 |  | 103 | 100 |
|  | 30 |  | 102 | 100 |
|  | 40 |  | 99 | 97 |
| Total impurities (% wt. over voriconazole wt.) | 2 to 8 | 0 | 0 | 0 |
|  | 25 |  | 0.002 | 0.01 |
|  | 30 |  | 0.004 | 0.018 |
|  | 40 |  | 0.019 | 0.069 |
| Particulate matter (PFAT) (%) | 2 to 8 | 0.005 | 0.003 | 0.002 |
|  | 25 |  | 0.002 | 0.002 |
|  | 30 |  | 0.002 | 0.001 |
|  | 40 |  | 0.001 | 0.003 |

*C&OP: Clear and one-phase solution

The stability results indicate that voriconazole is stable in the F145V LMBW composition. In contrast the currently marketed voriconazole drug which is in a lyophilized cyclodextrin-solubilized formulation (VFEND®), LMBW can provide a new formulation for voriconazole which liquid and ready-to-use is, i.e. does not require reconstitution with water before injection or dilution with an IV Infusion fluid.

Example 24

To further improve the stability of voriconazole in the LMBW, voriconazole and sucrose as a lyoprotectant or bulking agent were dissolved in a LMBW vehicle (F145V in example 18) to obtain a clear solution containing 30 mg/mL voriconazole and 8% sucrose. The solution was passed through a 0.1-micron filter, filled into glass vials and lyophilized to obtain an anhydrous LMBW or lyophilized and LMBW-solubilized voriconazole formulation. The lyophilized formulation is substantially free of water. The lyophilized formulation can be dissolved (reconstituted) in water quickly within 1-2 minutes to form a clear and one-phase solution and the solution can be diluted with IV Infusion Fluid without any precipitation. Therefore, an LMBW can be provided in the anhydrous form which can be readily dissolved in water to form clear and one-phase solution or a ready-to-use liquid formulation.

Example 25

This study is to develop a new aqueous formulation containing at least 15 mg/mL diazepam which is 3 times higher than the marketed injectable formulation ("Diazepam injection USP, 5 mg/mL") in order to deliver 10-20 mg diazepam in about 1-1.5 mL volume, which is desired for subcutaneous and intramuscular injection. Ninety-five (95) different aqueous compositions (coded as F1-F95) were designed, prepared and tested for diazepam solubility. These compositions contained almost all excipients or solubilizers that are the currently approved by FDA for subcutaneous and intramuscular injections. For each composition, diazepam was added to about 1-2% wt, mixed well with an aqueous vehicle containing one or more excipients, allowed for equilibration at RT, passed through a 0.2- or 0.45-micron filter to removed undissolved diazepam, and analyzed for diazepam concentration (solubility) by HPLC. The tables below list all compositions and the diazepam solubility test results. Some measured solubility values are reported in mg/g which is very close to mg/mL since all the compositions have a density close to 1 mg/mL.

| | Composition (% wt) | | | | | | | | | |
|---|---|---|---|---|---|---|---|---|---|---|
| Code | F1 | F2 | F3 | F4 | F5 | F6 | F7 | F8 | F9 | F10 |
| Diazepam | 1 | 1 | 2 | 2 | 4 | 4 | 1 | 1 | 1 | 1 |
| Sesame Oil | 10 | 5 | 10 | 5 | 10 | 5 | 15 | 5 | 10 | 0 |
| MCT | 0 | 5 | 0 | 5 | 0 | 5 | 0 | 0 | 0 | 5 |
| Egg lecithin | 10 | 10 | 10 | 10 | 10 | 10 | 5 | 15 | 10 | 15 |
| Sucrose | — | — | — | — | — | — | 0 | 0 | 10 | 0 |
| Water | 79 | 79 | 78 | 78 | 76 | 76 | 79 | 79 | 69 | 79 |
| Diazepam Solubility (mg/g) | 5.6 | 7.3 | 4.4 | 4.2 | Precipitation | | 3.2 | 9.7 | 9.7 | 7.7 |
| Type of formulation | Emulsion | | | | | | | | | |

| | Composition (% wt) | | | | | | | | | |
|---|---|---|---|---|---|---|---|---|---|---|
| Code | F11 | F12 | F13 | F14 | F15 | F16 | F17 | F18 | F19 | F20 |
| Diazepam | 1 | 1 | 1 | 1 | 1 | 1 | 1 | 1 | 1 | 1.5 |
| Sesame Oil | 0 | 0 | 0 | 5 | 2.5 | 2.5 | 3 | 3 | — | — |
| MCT | 10 | 15 | 10 | 0 | 2.5 | 2.5 | 0 | 0 | 2.5 | 2.5 |
| Egg lecithin | 10 | 5 | 10 | 15 | 15 | 15 | 22 | 22 | 10 | 15 |
| Sucrose | 0 | 0 | 10 | 8.2 | 0 | 8.2 | 0 | 8.2 | 8.2 | 8.2 |
| EDTA disodium | — | — | — | — | — | — | — | — | 0.0055 | 0.0055 |
| Water | 79 | 79 | 69 | 71.8 | 80 | 71.8 | 75 | 66.8 | 78.3 | 72.8 |
| Diazepam Solubility (mg/g) | 6.7 | 4 | 9.4 | 7 | 6.6 | 8 | 8.9 | 8.6 | 4.1 | 6.2 |
| Type of formulation | Emulsion | | | | | | | | | |
| pH | 6.7 | 4 | 9.4 | | | | | | | |

| | Composition (% wt) | | | | | | | | | |
|---|---|---|---|---|---|---|---|---|---|---|
| Code | F21 | F22 | F23 | F24 | F25 | F26 | F27 | F28 | F29 | F30 |
| Diazepam | 2 | >1 | >1 | >1 | >1 | >1 | >1 | >1 | >1 | >1 |
| Sesame Oil | — | 2.5 | 1 | 1 | 1 | 1 | 2 | 2 | 0 | 0 |
| MCT | 2.5 | 2.5 | 0 | 0 | 0 | 0 | 0 | 0 | 0 | 0 |
| E-80 | 20 | 10 | 5 | 10 | 15 | 20 | 5 | 10 | 5 | 10 |
| Sucrose | 8.2 | 8.2 | 0 | 0 | 0 | 0 | 0 | 0 | 0 | 0 |
| EDTA disodium | 0.0055 | 0.0055 | 0.0055 | 0.0055 | 0.0055 | 0.0055 | 0.0055 | 0.0055 | 0.0055 | 0.0055 |
| Glycerin | — | — | 2.25 | 2.25 | 2.25 | 2.25 | 2.25 | 2.25 | 2.25 | 2.25 |
| Water | 67.3 | 75.8 | 90.7 | 85.7 | 80.7 | 75.7 | 89.7 | 84.7 | 91.7 | 86.7 |
| Diazepam Solubility (mg/g) | 7.8 | 5.7 | 2.1 | 4.8 | 7.6 | 10.0 | 2.5 | 5.1 | 2.2 | 5.6 |
| Type of formulation | Emulsion | | | | | | | | | |

| | Composition (% wt) | | | | | | | | | |
|---|---|---|---|---|---|---|---|---|---|---|
| Code | F31 | F32 | F33 | F34 | F35 | F36 | F37 | F38 | F39 | F40 |
| Diazepam | >1 | >1 | >1 | >1 | >1 | >1 | >1 | >1 | >1 | >1 |
| Sesame Oil | 5 | 5 | 5 | 5 | 10 | 10 | 10 | 5 | 10 | 0 |
| MCT | 0 | 0 | 0 | 0 | 0 | 0 | 0 | 0 | 0 | 0 |
| Egg lecithin | 5 | 10 | 15 | 20 | 10 | 15 | 20 | 25 | 25 | 25 |
| Sucrose | 0 | 0 | 0 | 0 | 0 | 0 | 0 | 0 | 0 | 0 |
| EDTA disodium | 0.0055 | 0.0055 | 0.0055 | 0.0055 | 0.0055 | 0.0055 | 0.0055 | 0.0055 | 0.0055 | 0.0055 |
| Glycerin | 2.25 | 2.25 | 2.25 | 2.25 | 2.25 | 2.25 | 2.25 | 2.25 | 2.25 | 2.25 |
| Water | 86.7 | 81.7 | 76.7 | 71.7 | 76.7 | 71.7 | 66.7 | 66.7 | 61.7 | 71.7 |
| Diazepam Solubility (mg/g) | 2.1 | 5.2 | 8.2 | 12.5 | 6.0 | 9.5 | 12.9 | 11.7 | 10.8 | 8.9 |
| Type of formulation | Emulsion | | | | | | | | | |

| | Composition (% wt) | | | | | | | | | |
|---|---|---|---|---|---|---|---|---|---|---|
| Code | F41 | F42 | F43 | F44 | F45 | F46 | F47 | F48 | F49 | F50 |
| Diazepam | 1 | >1.5 | >1.5 | >1.5 | >1.5 | >1.5 | >1.5 | >1.5 | >1.5 | >1.5 |
| Sesame Oil | 20 | 6 | 8 | 10 | 8 | 10 | 0 | 5 | 8 | 10 |
| MCT | 0 | 0 | 0 | 0 | 0 | 0 | 10 | 5 | 0 | 0 |
| Egg lecithin | 5 | 20 | 20 | 20 | 20 | 20 | 20 | 20 | 20 | 20 |
| Sucrose | — | — | — | — | 8.2 | 8.2 | 8.2 | 8.2 | 8.2 | 8.2 |
| EDTA disodium | 0.0055 | 0.0055 | 0.0055 | 0.0055 | 0.0055 | 0.0055 | 0.0055 | 0.0055 | — | — |
| Glycerin | 2.25 | 2.25 | 2.25 | 2.25 | — | — | — | — | — | — |
| Water | 71.7 | 71.7 | 69.7 | 67.7 | 63.7 | 61.7 | 61.7 | 61.7 | 63.8 | 61.8 |
| Diazepam Solubility (mg/g) | 4.8 | 9.1 | 11 | 14.8 | 13.3 | 15.5 | >15 | >15 | 15.9 | 17.4 |
| Type of formulation | Emulsion | | | | | | | | | |

| | Composition (% wt) | | | | | | | | | |
|---|---|---|---|---|---|---|---|---|---|---|
| Code | F51 | F52 | F53 | F54 | F55 | F56 | F57 | F58 | F59 | F60 |
| Diazepam | >1.5 | >1.5 | >1.5 | >1.5 | 1.7 | 1.7 | 1.7 | 1.7 | 1.7 | >2.0 |
| Sesame Oil | 5 | — | 4 | 4 | 8 | 8 | 8 | 4 | 4 | — |
| MCT | 5 | 10 | 4 | 4 | — | — | — | — | — | 16.9 |
| Egg lecithin | 20 | 20 | 10 | 15 | 20 | 20 | 20 | 20 | 20 | 8.85 |

-continued

| | | | | | | | | | | |
|---|---|---|---|---|---|---|---|---|---|---|
| Sucrose | 8.2 | 8.2 | 8.2 | 8.2 | 8.2 | 8.2 | 8.2 | 8.2 | 8.2 | 2 |
| EDTA disodium | — | — | — | — | 0.0055 | 0.0055 | 0.0055 | 0.0055 | 0.0055 | — |
| Cholesterol | — | — | 0.6 | 0.6 | — | — | — | — | — | — |
| 5% Vitamin E succinate | — | — | 0.3 | 0.3 | — | — | 0.3 | — | — | — |
| Polysorbate 80 | — | — | — | — | 0.3 | — | — | — | — | — |
| Poloxamer 188 | — | — | — | — | — | 0.2 | — | — | 0.2 | — |
| Water | 61.8 | 61.8 | 72.9 | 67.9 | 61.7 | 61.8 | 61.7 | 66.0 | 65.9 | 70.3 |
| Diazepam Solubility (mg/g) | 20.5 | 18.8 | 5.9 | 10.6 | PPT | 9.4 | PPT | 9.6 | 8.2 | 10.1 |
| Type of formulation | | | | | Emulsion | | | | | |

| | Composition (% wt) | | | | | |
|---|---|---|---|---|---|---|
| Code | F60 | F61 | F62 | F63 | F64 | F65 |
| Diazepam | 1.7 | 1.7 | 1.7 | 1.7 | 1.7 | 1.7 |
| Glycocholic acid | 8.85 | 8.85 | 8.85 | 2 | 5 | 10 |
| Egg lecithin | 17 | 17 | 17 | 1.2 | 1.2 | 10 |
| Sesame oil | 5 | 10 | 15 | | | |
| Soybean oil | | | | 10 | 10 | 10 |
| Benzyl alcohol | 1.6 | 1.6 | 1.6 | — | — | — |
| Sodium metabisulfite | 0.1 | 0.1 | 0.1 | — | — | — |
| Glycerin | — | — | — | 2.25 | 2.25 | 2.25 |
| NaOH/HCl | | | | Adjust pH to 7.5 | | |
| Water, added to final volume | 100 | 100 | 100 | 100 | 100 | 100 |
| Diazepam Solubility (mg/g) | | | | Not soluble (<10 mg/g) | | |
| Type of formulation | | | | Mixed micelle | | |

| | Composition (% wt) | | | | | | | | | |
|---|---|---|---|---|---|---|---|---|---|---|
| Code | F66 | F67 | F68 | F69 | F70 | F71 | F72 | F73 | F74 | F75 |
| Diazepam | >2.0 | >2.0 | >2.0 | >2.0 | 2 | 2 | 2 | 2 | 2 | 2 |
| Sesame oil | — | — | — | — | — | — | — | — | 0 | 0 |
| Soy lecithin | 16.9 | 16.9 | 16.9 | 16.9 | 15.0 | 12.4 | 11.5 | 6.8 | 16.9 | 16.9 |
| Glycocholic acid | 8.85 | 8.85 | 8.85 | 8.85 | 7.85 | 6.46 | 6.02 | 3.56 | 8.85 | 8.85 |
| Benzyl Alcohol | 2 | 5 | 5 | 5 | 2.3 | 2.3 | 5 | 5 | 4.5 | 4.5 |
| Alcohol | 6 | 6 | 6 | 6 | — | — | — | — | 6.1 | 6.1 |
| Anhydrous alcohol | — | — | — | — | — | — | 6 | 6 | — | — |
| MCT | — | — | 2.5 | 5 | — | — | — | 5 | 7.5 | 10 |
| Myij S40 | — | — | — | — | 14 | 7 | 14 | 14 | — | — |
| Water | add to 100 | add to 100 | add to 100 | add to 100 | add to 100 | add to 100 | add to 100 | add to 100 | 40.3 | 37.8 |
| Diazepam Solubility (mg/mL) | 12.1 | 8.1 | 12.9 | 19.3 | 10 | 8.8 | 14.6 | 22.5 | 19.4 | 17.4 |
| pH | 7.6 | 7.6 | 7.6 | 7.7 | | | | | 7.5 | 7.5 |
| Type of formulation | Mixed micelle | | LMBW | | Mixed micelle | | | | LMBW | |

| | Composition (% wt) | | | | | | | | | | |
|---|---|---|---|---|---|---|---|---|---|---|---|
| Code | F76 | F77 | F78 | F79 | F80 | F81 | F82 | F83 | F84 | F85 | F86 | F87 |
| Diazepam | 2 | 2 | 2 | 2 | 1.7 | 1.7 | 1.7 | 1.7 | 1.7 | 1.7 | 1.7 | 1.7 |
| Sesame Oil | — | — | 5 | 10 | — | — | — | — | — | — | — | — |
| Soy lecithin | 16.9 | 16.9 | 16.9 | 16.9 | 16.9 | 16.9 | 18.6 | 20.3 | 20.3 | 20.3 | 22 | 22 |
| Glycocholic acid | 8.85 | 8.85 | 8.85 | 8.85 | 8.9 | 8.9 | 9.7 | 10.6 | 10.6 | 10.6 | 11.5 | 11.5 |
| Benzyl Alcohol | 4.5 | 4.5 | 4.5 | 4.5 | 4.5 | 4.5 | 4.5 | 4.5 | 4.5 | 9 | 4.5 | 9 |
| Alcohol | 6.1 | 6.1 | 6.1 | 6.1 | — | — | — | — | — | — | — | — |
| Anhydrous Alcohol | — | — | — | — | 6.1 | 0 | 6.1 | 6.1 | 0 | 0 | 6.1 | 0 |
| MCT | 12.5 | 15 | 0 | 0 | 6.5 | 6.5 | 6.5 | 6.5 | 6.5 | 6.5 | 6.5 | 6.5 |
| 1N NaOH | 20 | 20 | 20 | 20 | | | | | | | | |
| Water | 35.3 | 32.8 | 42.8 | 37.8 | 55.4 | 61.5 | 52.9 | 50.3 | 56.4 | 51.9 | 47.7 | 49.3 |
| Diazepam Solubility (mg/mL) | 16.3 | 15.4 | 8 | 7.3 | 15.9 | n/a | 16.1 | 17.6 | n/a | n/a | 17.3 | n/a |
| pH | 7.5 | 7.5 | 7.5 | 7.5 | 7.5 | 7.5 | 7.5 | 7.5 | 7.5 | 7.5 | 7.5 | 7.5 |
| Type of formulation | LMBW | | LMBW-like, where MCT is replaced by LCT | | | | | LMBW | | | | |

| | Composition (% wt) | | | | | | | | | |
|---|---|---|---|---|---|---|---|---|---|---|
| Code | F83-2 | F88 | F89 | F90 | F91 | F92 | F93 | F94 | F95 | Diazepam Injection, USP |
| Diazepam | 1.7 | 1.7 | 1.7 | 1.7 | 1.7 | 1.7 | 1.7 | 1.7 | 1.7* | 0.5 |
| Soy Lecithin | 20.3 | 20.3 | 20.3 | 20.3 | 20.3 | 20.3 | 20.3 | 20.3 | 20.3 | 0 |
| Glycocholic acid | 10.6 | 10.6 | 10.6 | 10.6 | 10.6 | 10.6 | 10.6 | 10.6 | 10.6 | 0 |
| Propylene glycol | 0 | 0 | 0 | 0 | 0 | 0 | 0 | 0 | 0 | 40 |
| Sodium benzoate | 0 | 0 | 0 | 0 | 0 | 0 | 0 | 0 | 0 | 5 |
| Benzyl alcohol | 4.5 | 4.5 | 4.5 | 4.5 | 4.5 | 4.5 | 4.5 | 4.5 | 4.5 | 1.5 |
| Ethanol | 6.1 | 6.1 | 6.1 | 6.1 | 6.1 | 6.1 | 6.1 | 6.1 | 6.1 | 10 |

-continued

| | | | | | | | | | | |
|---|---|---|---|---|---|---|---|---|---|---|
| MCT | 6.5 | 6.5 | 6.5 | 6.5 | 6.5 | 6.5 | 6.5 | 6.5 | 6.5 | — |
| EDTA disodium, 2H$_2$O | — | 0.2 | — | — | — | — | — | — | 0.06 | — |
| EDTA calcium disodium, 2H$_2$O | — | — | 0.34 | — | — | — | — | — | — | — |
| Sodium metabisulfite | — | — | — | 0.3 | — | — | — | — | — | — |
| Methionine | — | — | — | — | 0.15 | 0 | 0 | 0 | 0.15 | — |
| Cysteine | — | — | — | — | — | 0.1 | — | — | — | — |
| Ascorbic acid | — | — | — | — | — | — | 1 | — | — | — |
| Monothioglycerol | — | — | — | — | — | — | — | 0.5 | — | — |
| DI Water, add to | 100 | 100 | 100 | 100 | 100 | 100 | 100 | 100 | 100 | 100 |
| N$_2$ gas (in vial headspace) | Yes | Yes | Yes | Yes | Yes | Yes | Yes | Yes | Yes | N/A |
| pH | 7.2 | 7.2 | 7.2 | 7.3 | 7.3 | 7.2 | 7.2 | 7.3 | 7.5 | 6.6 |
| Appearance | Clear & one-phase | | | | | Hazy | Clear & one-phase | | | |
| Diazepam Solubility (mg/mL) | 17.5 | 17 | 17.2 | 16.6 | 16.9 | n/a | 16.6 | 17.4 | 17.0 | 4.9 |
| Type of formulation | LMBW | | | | | | | | | Co-solvent |

Among all the compositions tested including emulsion, mixed micelle, LMBW and co-solvent formulation, only the LMBW compositions were able to dissolve diazepam to a greater than 15 mg/mL concentration, indicating the LMBW is a most effective solubilizer than an emulsion, mixed micelle or a co-solvent vehicle. Except F92, all diazepam containing LMBW solutions were clear and one-phase at a neutral pH. One of them (F95) was selected for further development and testing in human (Example 15).

Example 26

The F95 LMBW containing 17 mg/mL diazepam was compared with Diazepam Injection USP (5 mg/mL) for stability. Vialed F95 and Diazepam Injection USP were stored at 25° C. for 6 months and tested for stability, including appearance, pH, diazepam assay, purity and impurity by HPLC. The results are shown in the table below:

| | Test | | | |
|---|---|---|---|---|
| | LMBW (F95) | | Diazepam injection USP | |
| Appearance | Time 0 Clear & one-phase solution | 6M Same | Time 0 Clear & one-phase solution | 6M Same |
| pH | 7.1 | 6.8 | 6.6 | N/D |
| Diazepam assay (mg/mL) | 18.0 | 17.6 | 5.02 | 5.0 |
| Diazepam assay recovery (% over the Time 0 value) | 100 | 97.6 | 100 | 96.2 |
| Diazepam purity (% HPLC peak area) | 100 | 100 | 100 | 99.9 |
| Diazepam Related Compound A (% HPLC peak area) | Not detected | Not detected | Not detected | 0.15 |

Diazepam in F95 LMBW is more stable than in the marketed Diazepam Injection, USP formulation.

Example 27

The aim of this study was to determine solubility of insoluble drugs in 16% sulfobutyl ether beta cyclodextrin (SBECD) aqueous solution and compare the results to their solubilities obtained in F96 LMBW (Example 4). Twenty-one (21) insoluble drugs having a wide variety of chemical structures (including chemical element, small molecule, peptide and protein), properties and biological activities (including drugs, diagnostic agents and nutritional supplement agents) were selected and tested for solubility in 16% SBECD as follows:

1. Measure out a fixed amount of 16% SBECD aqueous.
2. Add a known amount of an insoluble drug substance.
3. Mix to dissolve the drug substance.
4. If the drug substance has completely dissolved, repeat Steps 1-3 until 16% SBECD can no longer dissolve the added drug substance.
5. Record the maximum amount of the insoluble drug substance that 16% SBECD could dissolve and use this value to calculate the drug's solubility in the 16% SBECD.

| Drug Name | Measured solubility in F96 LMBW Vehicle (mg/mL) | Measured solubility in 16% SBECD (mg/mL) |
|---|---|---|
| Amiodarone | 118 | 9.25 |
| Amphotericin | 2.4 | 0.07 |
| Aprepitant | 12.7 | 0.15 |
| Camptothecin | 0.5-1 | 0.06 |
| Casein (protein) | 1 | 0.15 |
| Clarithromycin | 9.1 | 1.71 |
| Cyclosporine (peptide) | 8.1 | 0.11 |
| Celecoxib | 7.3 | 1.03 |
| Ibuprofen | 53.1 | 3.58 |
| Intraconazole | 0.5-1 | 0.17 |
| Iodine (element) | 4 | Not soluble (<1) |
| Irinotecan HCl | 20.4 | 2.12 |
| Levodopa | 10 | 2.13 |
| Paclitaxel | 1 | 0.13 |
| Phytonadione | 28.2 | 0.15 |
| Posaconazole | 0.5 | 0.27 |
| Prednisolone acetate | 1 | 1.61 |
| Progesterone | 12.0 | 4.06 |
| Propofol | 50.8 | 56.6 |
| Resveratrol | 9 | 4.85 |
| Tyrosine (amino acid) | 1 | 0.85 |
| Voriconazole | 20 | 8.60 |

Except prednisolone acetate and propofol, all above drugs has much higher solubility in F96 LMBW vehicle than in 16% SBECD. These findings demonstrate that for most of the insoluble drugs tested (20/22), the LMBW is a better solubilizers than SBECD. The fact that a single LMBW (F96) solubilized (to ≥1 mg/mL) all the insoluble drugs (22/22) with widely different structures, whereas SBECD can only selectively solubilize a few of them (11/22), further supports that LMBWs are Universal Solubilizers.

Example 28

Figure 7:
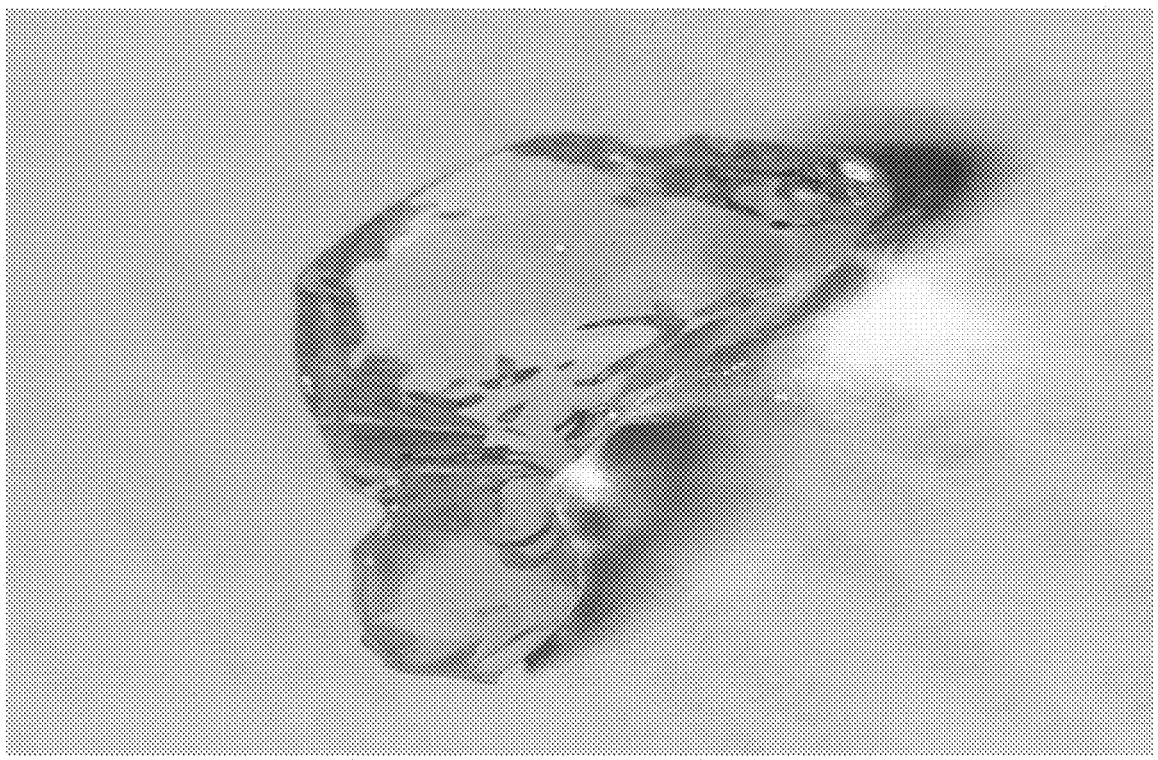
Figure 8A:
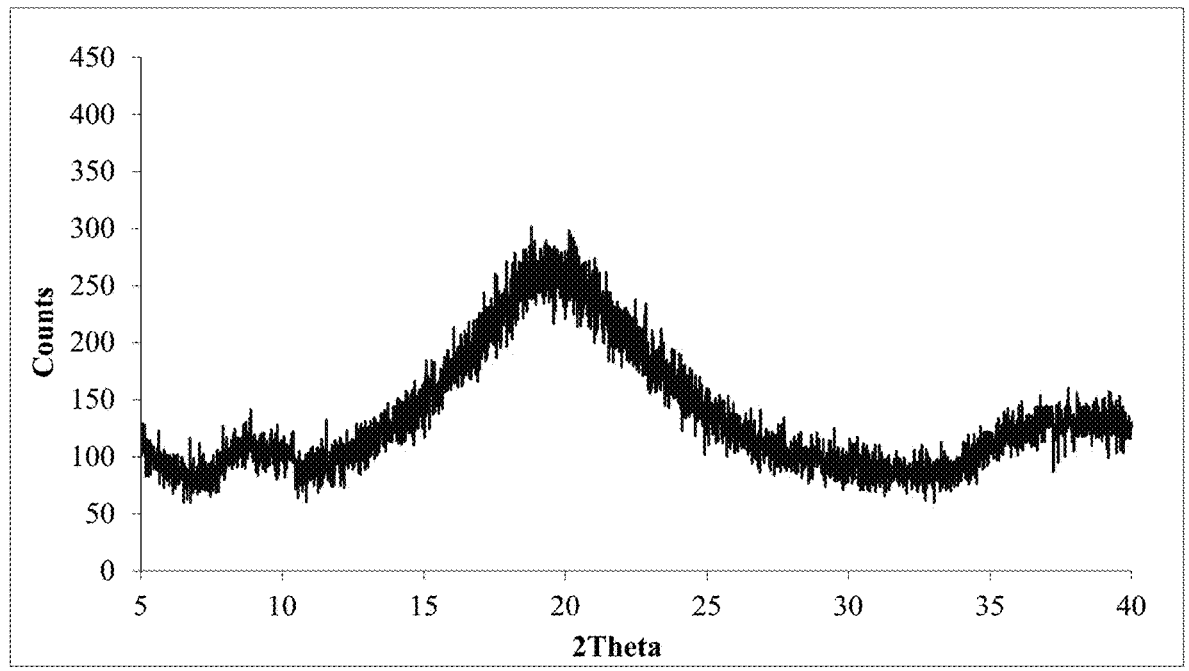
FIGS. 8A and 8B illustrate the XRPD spectrum of an amorphous Solid LMBW (F95, Example 28) in the upper panel (8A) in comparison with a crystalline Physical Mixture having the same components as the Solid LMBW but prepared by direct mixing of the components in the lower panel (8B).
Figure 8B:
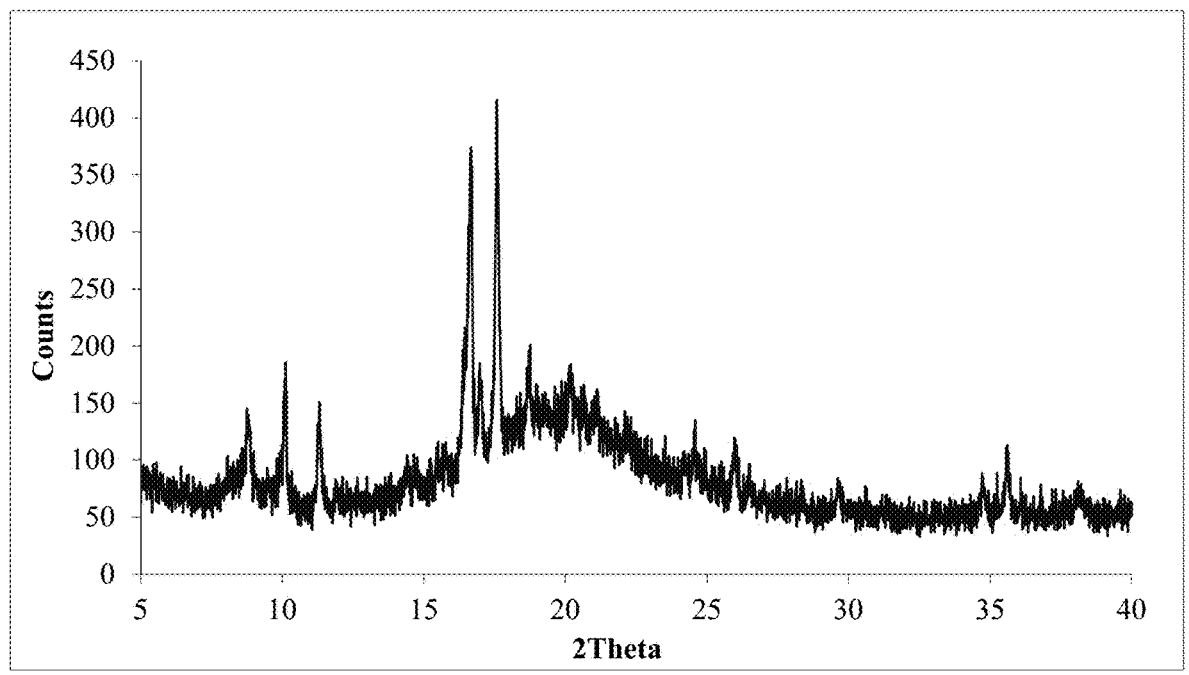

The aim of this experiment was preparing a Solid LMBW and to characterize its physical structure and morphology. The F95 LMBW composition as shown in Example 16 was prepared, divided into several portions, each portion was adjusted to a pH between 5.5 and 7.0, then freeze-dried to remove the water and ethanol. The dried or Solid LMBW (F95) were amber-colored, transparent glass-like solid when the pH was 5.5. Haziness in the solid was observed in the higher pH samples with the higher pH showed more haziness. For comparison, a physical mixture was prepared by direct mixing of lecithin, MCT and bile salt at the same L/M/B ratio as in F95. Both F95 Solid LMBW and the physical mixture were tested for appearance, XRPD and DSC/TGA. F95 Solid LMBW was a transparent glass-like solid (FIG. 7) while the physical mixture was an oily and opaque paste. X-ray powder diffraction (XRPD) is a powerful method for the study of crystalline and partially crystalline solid-state materials. There was no crystalline feature observed for Solid LMBW (F95) by XRPD. In contrast, the physical mixture's XRPD spectra displayed distinctive crystalline peaks (FIG. 8). The XRPD results suggest that Solid LMBW is an amorphous glass while the physical mixture has certain crystalline structures. Upon heating, Solid LMBW (F95) became softer with increased temperature and eventually liquified. Upon mixing with water, Solid LMBW (F95) dissolves rapidly and turned into a clear and one-phase LMBW solution.

These findings suggest that (1) a Solid LMBW is unique in its physical structure and such structure can't be obtained by simple mixing of all its components, (2) the disclosed process of making LMBW and the subsequent removal of water and alcohol to obtain the Solid LMBW have created a unique complex among lecithin, MCT and bile salt and such complex is transparent and amorphous, (3) the Solid LMBW can be used as a solid vehicle or matrix to dissolve insoluble drugs while permitting is use in a solid dosage form such as tablet or capsule, and (4) the melting feature of the Solid LMBW is well suited for hot melt or hot melt extrusion which are useful technique to incorporate a drug substance into a solid matrix for improved drug solubility, dissolution or absorption.

Example 29

The aim of this study was to demonstrate the utility of the F95 LMBW vehicle of Example 3 in dissolving a range of insoluble solids that are related to certain human diseases, such as monosodium urate found in the gout joints, cholesterol in the atherosclerosis lesions or xanthelasma, beta-amyloid, which a protein deposit in the brains of Alzheimer's patients and fat under the skin which is undesirable for cosmetic reasons. These solids have very low solubility in the body fluids and therefore they have a high tendency to precipitate and to form the undesirable solid deposits in vivo. For each solid, the following procedure was used to determine its solubility in the F95 LMBW and in the phosphate buffered saline (PBS):
1. Weigh out a fixed amount of a solid of interest,
2. Add a known amount of F95 vehicle at pH 7,
3. Mix to dissolve the solid,
4. If the solid has completely dissolved, add more until it is no longer dissolving in the vehicle
5. Record the amount of F95 vehicle added and use the value to calculate the solubility of the solid in the F95 vehicle.

| Chemical Name | Related disease | Solubility in PBS (mg/mL) | Measured solubility in F96 LMBW Vehicle (mg/mL) |
|---|---|---|---|
| Mono sodium urate | Gout | <0.001 | 0.05 |
| Cholesterol | Atherosclerosis & xanthelasma | 0.05 | 25.0 |
| Fat (lard) | Wrinkles and cosmetic imperfection | <0.1 | 8.0 |
| Beta-amyloid protein fragments (1-42) | Alzheimer's disease | 0.5 | 0.7 |

All test solids have very low solubility in PBS which resembles a biological fluid. F96 LMBW can increase their solubility significantly in water and therefore potentially be used as a remover for these undesirable solid deposits in vivo.

What is claimed is:

1. An injectable solubilizer composition, comprising:
   a. soy lecithin, having phosphatidylcholine content no less than 75% w/w based on the lecithin weight, at a concentration between about 6% and about 72.5%;
   b. a medium chain triglyceride (MCT) having fatty acids of chain length of about 6 to 12 carbons, at a concentration between 2% and about 32.5%;
   c. a bile salt at a concentration between about 11.5% and 90%;
   d. water, and
   e. optionally alcohol, where the % is the weight percentage over the total weight of soy lecithin, MCT and bile salt, and where the said composition is a clear and one-phase aqueous solution and is substantially free of solid particles or oil droplets.

2. The composition according to claim 1, wherein the weight/weight ratio of water to the total weight of soy lecithin, MCT and bile salt is no less than about 0.1/1.

3. The composition according to claim 1, where the composition is substantially free of liposome, emulsion, phospholipid particles or oil droplets of size greater than 5 nanometers in diameter.

4. The composition according to claim 1, wherein the MCT is derived from a natural source or is synthetically made.

5. The composition according to claim 1, wherein the bile salt is selected from a group consisting of sodium, potassium, lithium, calcium, arginine, lysine or ammonium salts of cholic acid, glycocholic acid, taurocholic acid, deoxycholic acid, glyco- or taurodeoxycholic acid, chenodeoxycholic acid, glyco- or taurochenoxydeoxycholic acid, or a mixture thereof.

6. The composition according to claim 1, that further contains an alcohol selected from a group consisting of ethanol, benzyl alcohol, propylene glycol, polyethylene glycol of a low molecular weight ranging from 100-5,000 or a combination thereof.

7. The composition according to claim 6, wherein the weight/weight ratio of alcohol to the total weight of soy lecithin, MCT and bile salt is no more than about 1.6/1.

8. The composition according to claim 1, wherein the composition is an amorphous solid.

9. The composition according to claim 1, further containing an insoluble or soluble drug.

10. The composition according to claim 9, wherein the drug is selected from a group consisting of small molecules, peptides, proteins or a combination thereof.

11. The composition according to claim 9, that contains one or more insoluble drug(s) selected from a group consisting of amiodarone, amphotericin, aprepitant, camptothecin, cannabidiol, casein, celecoxib, clarithromycin, cyclosporine, diazepam, docetaxel, ibuprofen, iodine, itraconazole, iodine, irinotecan, levodopa, paclitaxel, phytonadione, posaconazole, prednisolone acetate, progesterone, propofol, resveratrol, tetrahydrocannabinol, tyrosine, voriconazole, PGE2, PGE1, opalmon, piroxicam, benexate, dexamethasone, nitroglycerin, cefotiam-hexetil, cephalosporin, tiaprofenic acid, diphenhydramin and chlortheophyllin, chlordiazepoxide, hydrocortisone, cisapride, nimesulide, alprostadil, nicotine, chloramphenicol, diclofenac sodium, estradiol, indomethacin, omeprazol, ziprasidone, dextromethorphan, cetirzine, mitomycin, meloxicam, aripiprazole or salt thereof.

12. The composition according to claim 1, further comprising voriconazole at a concentration between 0.01% and about 3%, soy lecithin at a concentration between about 6% and about 72.5%, MCT at a concentration between 2% and about 32.5%, glycocholic acid at a concentration between about 11.5% and 90%, wherein the % is the weight percentage over the total weight of soy lecithin, MCT and glycocholic acid, and pH of the solution is between 3.5 and 7.5.

13. The composition according to claim 1, further comprising diazepam at a concentration between 0.01% and about 3%, soy lecithin at a concentration between about 6% and about 72.5%, MCT at a concentration between 2% and about 32.5%, glycocholic acid at a concentration between about 11.5% and 90%, wherein the % is the weight percentage over the total weight of soy lecithin, MCT and glycocholic acid, and pH of the solution is between 6 and 8.5.

14. The composition of claim 13, wherein the composition has at least one of the following pharmacokinetic parameters following a subcutaneous injection of a 10 mg diazepam dose into humans:
(a) $AUC_{(0-t)}$ is about 6194 ng×h/mL
(b) $AUC_{(0-inf)}$ is about 6688 ng×h/mL, and
(c) $C_{max}$ is about 122.65 ng/mL.

15. The composition according to claim 1, wherein the pH of the composition is between 3 and 10.

16. The composition according to claim 1, that further contains:
a) a preservative selected from a group consisting of cresols, phenol, benzyl alcohol, ethanol, chlorobutanol, parabens, imidura, benzylkonium chloride, EDTA or a salt or a combination thereof; or
b) a bulking agent selected from a group consisting of mannitol, sorbitol, xylitol, lactose, fructose, xylose, sucrose, trehalose, mannose, maltose, dextrose, dextran, dextrin, or a combination thereof; or
c) an antioxidant selected from: EDTA, citric acid, glycine, butylated hydroxyanisole, butylated hydroxytoluene, cysteine, methionine, thioglycerol, bisulfate, metabisulfate, ascorbate, propyl gallate, tocopherol, reducing sugar, or a salt or combination thereof.

17. The composition according to claim 1, wherein said composition is suitable for administration to a human or animal subject by oral administration, injection through a needle, instillation through a catheter, or applications onto the skin, mucous membranes, in wounds, into the eyes, ears, vagina, urethra or rectum.

18. The composition according to claim 12, wherein said composition has a light transmittance (T800) of no less than 80%; or wherein said composition has a viscosity in a range between about 10 and 1000 cP.

19. A method for preparation of a composition, comprising:
(a) dissolving soy lecithin to a concentration between about 6% and about 72.5%, a medium chain triglyceride (MCT) to a concentration between 2% and about 32.5% and a bile salt to a concentration between about 11.5% and 90%, all in weight percent over the total weight of soy lecithin, MCT and bile salt, in water, wherein the weight/weight ratio of water to the total amount of soy lecithin, MCT and bile salt is no less than about 0.1/1, to form a clear one-phase aqueous solution composition, and
(b) adjusting pH to between 3 and 10.

* * * * *